United States Patent
Pastor et al.

(10) Patent No.: US 6,410,733 B1
(45) Date of Patent: Jun. 25, 2002

(54) AMIDINE INHIBITORS OF SERINE PROTEASES

(75) Inventors: Richard M. Pastor, San Francisco; Dean R. Artis, Kensington; Alan G. Olivero, Half Moon Bay, all of CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 09/947,424

(22) Filed: Sep. 5, 2001

Related U.S. Application Data

(60) Provisional application No. 60/231,679, filed on Sep. 11, 2000.

(51) Int. Cl.$^7$ .................... C07D 215/14; C07D 207/09; A61K 31/47; A61K 31/40
(52) U.S. Cl. ................. 546/168; 546/208; 548/537; 548/546; 514/423; 514/424; 514/306; 514/326
(58) Field of Search .................... 548/537, 546; 514/423, 424, 306, 326; 546/168, 308

(56) References Cited

U.S. PATENT DOCUMENTS

| | | |
|---|---|---|
| 5,504,064 A | 4/1996 | Morrissey et al. |
| 5,504,067 A | 4/1996 | Morrissey et al. |
| 5,580,560 A | 12/1996 | Nicolaisen et al. |
| 5,589,173 A | 12/1996 | O'Brien et al. |
| 5,646,165 A | 7/1997 | Abelman et al. |
| 5,656,600 A | 8/1997 | Abelman et al. |
| 5,656,645 A | 8/1997 | Tamura et al. |
| 5,658,930 A | 8/1997 | Tamura et al. |
| 5,658,939 A | 8/1997 | Abelman et al. |
| 5,670,479 A | 9/1997 | Abelman et al. |
| 5,679,639 A | 10/1997 | Griffin et al. |
| 5,726,159 A | 3/1998 | Schacht et al. |
| 5,998,379 A * | 12/1999 | Gyorkos ............... 514/18 |
| 6,057,342 A | 5/2000 | Fevig et al. |
| 6,291,514 B1 * | 9/2001 | Illig et al. ............... 514/447 |

FOREIGN PATENT DOCUMENTS

| | | |
|---|---|---|
| WO | WO 93/15756 | 8/1993 |
| WO | WO 94/13693 | 6/1994 |
| WO | WO 96/10022 | 4/1996 |
| WO | WO 96/16940 | 6/1996 |
| WO | WO 96/40679 | 12/1996 |
| WO | WO 97/30073 | 8/1997 |
| WO | WO 99/64392 | 12/1999 |

OTHER PUBLICATIONS

Broze, George ., "Tissue Factor Pathway Inhibitor" *Thromb. Haemostas.* 74:90 (1995).

Dennis and Lazarus, "Kunitz Domain Inhibitors of Tissue Factor–Factor VIIA; II. Potent and Specific Inhibitors by Competitive Phage Selection" *Journal of Biological Chemistry* 269(35): 22137–22144 (1994).

Hagen et al., "Characterization of a cDNA coding for human factor VII" *Proc. Natl. Acad. Sci. USA* 83:2412–2416 (1986).

Harker et al., "Antithrombotic benefits and hemorrhagic risks of direct thrombin antagonists" *Thrombosis and Haemostasis* 74:464–472 (1995).

Jang et al., "Influence of blockade at specific levels of the coagulation cascade on restenosis in a rabbit atherosclerotic femoral artery injury model" *Circulation* 92:3041–3050 (1995).

Katakura, S. et al., "A novel factor Xa inhibitor: structure––activity relationships and selectivity between factor Xa and thrombin" *Biochem. & Biophys. Res. Comm.* 197:965–972 (1993).

Kelley et al., "A Soluble Tissue Factor Mutant Is a Selective Anticoagulant and Antithrombotic Agent" *Blood* 89(9):3219–3227 (1997).

Kirchhofer et al., "Active Site–Blocked Factors VIIa and IXa Differentially Inhibit Fibrin Formation in a Humam Ex Vivo Thrombosis Model" *Arterioslcer. Thromb. Vasc. Biol.* 15(8):1098–1106 (Aug. 1995).

Lawson, J. H. et al., "A model for the tissue factor pathway to thrombin" *Journal of Biological Chemistry* 269:23357–23366 (1994).

Stannssens et al., "Anticoagulant repertoire of the hookworm ancylostoma caninum" *Proc. Natl. Acad. Sci. USA* 93:2149–2154 (1996).

Stubbs and Bode, "Coagulation factors and their inhibitors" *Current Opinion in Structural biology* 4:823–832 (1994).

* cited by examiner

*Primary Examiner*—Floyd D. Higel
*Assistant Examiner*—Kamal Saeed
(74) *Attorney, Agent, or Firm*—David W Evans

(57) ABSTRACT

Inhibitors of serine proteases are provided having formula (I)

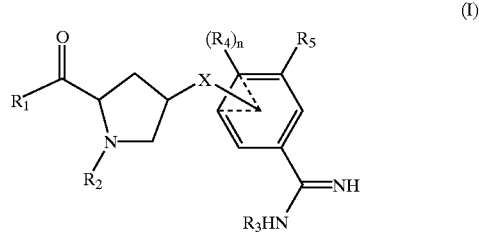

wherein X, $R_1$, $R_2$, $R_3$, $R_4$ and $R_5$ are as defined herein. In particular, the compounds bind to factor VIIa, tissue factor/factor Xa complex, thrombin, trypsin, plasmin and kallikrein and have anticoagulant activity. Pharmaceutical compositions comprising the compounds are useful for inhibiting the formation of veinous and/or arterial thrombi in vivo.

20 Claims, No Drawings

AMIDINE INHIBITORS OF SERINE PROTEASES

This application claims benefit of U.S. Provisional Application No. 60/231,679 filed on Sep. 11, 2000.

FIELD OF THE INVENTION

The invention relates to novel compounds which are inhibitors of serine proteases such as tissue factor (TF)/factor VIIa, factor Xa, thrombin and/or kallikrein, as well as pharmaceutical compositions containing these compounds which are useful for inhibiting serine proteases and for treating disorders mediated thereby.

BACKGROUND OF THE INVENTION

Normal haemeostasis is the result of a complex balance between the processes of clot initiation, formation and dissolution. The complex interactions between blood cells, specific plasma proteins and the vascular surface, maintain the fluidity of blood, however in the case of injury, blood coagulation is vital for the containment of bodily fluids and is an important component of host defense mechanisms. Many significant disease states are related to abnormal clot formation (thrombosis) in blood vessels. For example, in arterial vasculature abnormal thrombus formation due to deterioration of an established atherosclerotic plaque is a major cause of acute myocardial infarction and unstable angina. In venous vasculature, many patients undergoing surgery, particularly in the abdominal and lower body regions, experience thrombus formation which reduces blood flow and can lead to a pulmonary embolism. Disseminated intravascular coagulopathy in both the venous and arterial systems occurs commonly during septic shock, some viral infections and cancer which often leads to rapid and widespread thrombus formation and organ failure.

Coagulation and clotting (thrombus formation) involves the sequential activation of multiple zymogens in a process leading to thrombin generation which in turn is responsible for the conversion of fibrinogen to an impermeable cross-linked fibrin clot. Thrombin production is the result of a blood coagulation cascade which has been intensively studied and increasingly characterized. See for example, Lawson, J. H., et al. (1994) J. Biol. Chem. 269:23357. The coagulation reactions of this cascade involve initiation, amplification and propagation phases. Additionally, the cascade has been divided into extrinsic and intrinsic pathways. The intrinsic pathway involves factors XII, XI, and IX and leads to the formation of a complex of factor IXa with its cofactor, factor VIIIa. This complex converts factor X to Xa. Factor Xa is an enzyme which forms a complex with its cofactor, factor Va, and rapidly converts prothrombin to thrombin. Thrombin in turn converts fibrinogen to fibrin monomers which polymerize to form a clot. The extrinsic pathway involves factor VIIa and tissue factor, which form a complex (TF/factor VIIa), and convert factor X to Xa. As in the intrinsic pathway, factor Xa converts prothrombin to thrombin.

Thrombin (factor IIa), as noted above, occupies a central position in the coagulation cascade by converting fibrinogen to fibrin. Consequently, substantial synthetic efforts have been directed to the development of compounds that bind to thrombin in order to inhibit its activity such as N-arylsulfinated phenylalanine amides. Additional compounds which have been prepared as synthetic thrombin inhibitors are disclosed in U.S. Pat. No. 5,656,600; U.S. Pat. No. 5,656,645; U.S. Pat. No. 5,670,479; U.S. Pat. No. 5,646,165; U.S. Pat. No. 5,658,939; U.S. Pat. No. 5,658,930 and WO 97/30073. Many thrombin inhibitors have been designed to mimic the structure of hirudin, a protein produced by medicinal leeches (Hirudo medicinalis), which binds to thrombin thereby inhibiting coagulation. Stubbs and Bode, *Current Opinion in Structural Biology* 1994, 4:823–832. Further synthetic thrombin inhibitors are reported in *Annual Reports in Medicinal Chemistry*, 1995–1997, Academic Press, San Diego, Calif.

TF/factor VIIa is a serine protease complex that participates in blood coagulation by activating factor X and/or factor IX. Factor VIIa is produced from its precursor, factor VII, which is synthesized in the liver and secreted into the blood where it circulates as a single chain glycopeptide. The cDNA sequence for factor VII has been characterized (Hagen et al., 1986, Proc. Natl. Acad. Sci. U.S.A., 83:2412–2416). A variety of natural and synthetic inhibitors of TF/factor VIIa are known and have varying potency and selectivity such as those disclosed in U.S. Pat. No. 5,589,173 used to treat myocardial infarction. Tissue factor pathway inhibitor (TFPI; Broze, 1995, Thromb. Haemostas., 74:90) and nematode anticoagulant peptide c2 (NAPc2; Stanssens et al., 1996, Proc. Natl. Acad. Sci. U.S.A., 93:2149) bind factor Xa prior to the formation of a quaternary inhibitory complex with the TF/factor VIIa complex. Small protein direct inhibitors (Dennis et al, 1994, J. Biol. Chem., 35:22137) and inactive forms of TF/factor VIIa are also known (Kirchhofer et al, 1995, Arteriosclerosis, Thrombosis and Vascular Biol., 15:1098; Jang et al, 1995, Circulation, 92:3041). Additionally, synthetic peptides and soluble forms of mutant TF which retain binding affinity but have reduced cofactor activity have been prepared (Roenning et al, 1996, Thromb. Res., 82:73; Kelley et al, 1997, Blood, 89:3219). U.S. Pat. No. 5,679,639 describes polypeptides and antibodies which inhibit serine protease activity. U.S. Pat. No. 5,580,560 describes a mutant factor VIIa which has an improved half-life. U.S. Pat. No. 5,504,067 and U.S. Pat. No. 5,504,064 describe a truncated TF for the treatment of bleeding. Kunitz domain-tissue factor fusion proteins have also been shown to be bifunctional anticoagulants (Lee et al, 1997, Biochemistry, 36:5607–5611). The TF/factor VIIa complex has been indicated as an attractive target for the development of inhibitors based on a dissociation between surgical bleeding and prevention of intravascular thrombosis (Harker et al, 1995, Thromb. Haemostas., 74:464).

Factor Xa is also central to thrombosis since it is a product of both the intrinsic and extrinsic coagulation pathways. Inhibitors of factor Xa have been synthesized such as bisamidine compounds (Katakura, S. (1993) Biochem. Biophys. Res. Commun., 197:965), compounds based on the structure of arginine (WO 93/15756; WO 94/13693) and phenyl and naphthylsulfonamides (WO 96/10022; WO 96/16940; WO 96/40679).

Percutaneous transluminal coronary angioplasty (PTCA) and recanalization are favored procedures for treating occluded vessels. However, arterial thrombosis following these procedures remains a leading cause of failure. Anticoagulants including heparin, the most widely used anticoagulant, have not been shown to be entirely effective or safe in the treatment and prevention of acute arterial thrombosis or rethrombosis. Accordingly, there remains a need for compounds which are effective inhibitors of enzymes in the coagulation cascade and which exhibit improved inhibitory activity and/or selectivity towards selected enzymes in the cascade.

SUMMARY OF THE INVENTION

In an aspect of the present invention, there is provided novel compounds of formula (I) A compound of formula (I)

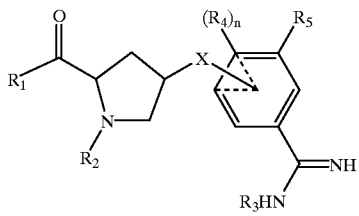

(I)

wherein
- X is O, CR$_6$R$_{6'}$, NR$_6$, S, wherein R$_6$ and R$_{6'}$ are independently H or alkyl;
- R$_1$ is H, —OR$_7$, an amino acid or —NR$_7$R$_{7'}$ wherein R$_7$ and R$_{7'}$ are independently H or a hydrocarbon chain, a carbocycle, a heterocycle, a carbocycle-substituted hydrocarbon chain or a heterocycle-substituted hydrocarbon chain optionally substituted with hydroxyl, halogen, cyano, amino, nitro, amidine, guanidine alkyl, halo-substituted alkyl, alkoxy, aryl or carboxyl; or R$_7$ and R$_{7'}$ together form a heterocycle optionally fused to another heterocycle or carbocycle wherein said heterocycle and carbocycle are optionally substituted with hydroxyl, halogen, amino, nitro, amidine, guanidine, alkyl, halo-substituted alkyl, alkoxy or carboxyl;
- R$_2$ is H or a hydrocarbon chain, a carbocycle or a carbocycle-substituted hydrocarbon chain optionally substituted with hydroxyl, oxo, halogen, cyano, amino, nitro, amidine, guanidine, alkyl, halo-substituted alkyl, alkoxy or carboxyl; and wherein said hydrocarbon chain is optionally interrupted with N, O, S, SO or SO$_2$;
- R$_3$ is H or a protecting group;
- R$_4$ is selected from the group consisting of H, hydroxyl, halogen, amino, nitro, amidine, guanidine and acylamino;
- R$_5$ is H or R$_4$ and R$_5$ together form a 5 or 6 member carbocycle or heterocycle ring optionally substituted with hydroxyl, halogen, amino, nitro, amidine, guanidine or acylamino;
- n is 0 or 1; and
- salts, solvates and hydrates thereof.

In another aspect of the invention, there is provided pharmaceutical compositions comprising a compound of the invention and a pharmaceutically acceptable carrier.

In another aspect of the invention, there is provided a method of treating a disease or condition mediated by a serine protease in a mammal comprising administering to said mammal an effective amount of a compound of the invention.

DETAILED DESCRIPTION OF THE INVENTION

The invention provides novel compounds of formula (I)

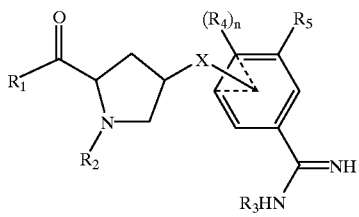

(I)

wherein X, R$_1$, R$_2$, R$_3$, R$_4$ and R$_5$ are as defined herein.

The term "amino acid" refers to naturally and non-naturally occurring α-(alpha), β-(beta), D- and L-amino acid residues. Preferred amino acid residues are hydrophobic such as alanine, β-alanine, phenylalanine, valine, leucine and isoleucine.

The term "hydrocarbon chain" refers to saturated, unsaturated, linear or branched carbon chains i.e. alkyl, alkenyl and alkynyl. Preferred hydrocarbon chains incorporate 1–12 carbon atoms, more preferably 1–6 and most preferably 1–4 carbon atoms i.e. methyl, ethyl, propyl, butyl and allyl.

The term "carbocycle" refers to a mono-, bi- or tri-cyclic carbon ring or ring system having 4–16 members which is saturated, unsaturated or partially unsaturated including aromatic ring systems. Preferred carbocyclic rings include cyclopentyl, cyclohexyl, phenyl and naphthyl.

The term "heterocycle" refers to a mono-, bi- or tri-cyclic ring system having 5–16 members wherein at least one ring atom is a heteroatom (i.e. N, O and S as well as SO, or SO$_2$). The ring system is saturated, unsaturated or partially unsaturated and may be aromatic. Preferred heterocycles include piperidine, piperazine, pyridine, pyrazine, pyrimidine, pyridazine, morpholine, pyran, pyrole, furan, thiophene (thienyl), imidazole, pyrazole, thiazole, isothiazole, dithiazole, oxazole, isoxazole, dioxazole, thiadiazole, oxadiazole, tetrazole, triazole, thiatriazole, oxatriazole, thiadiazole, oxadiazole, purine, and benzofused derivatives thereof.

X is O, CR$_6$R$_{6'}$, NR$_6$ or S, wherein R$_6$ and R$_{6'}$ are independently H or alkyl. In a particular embodiment X is O. In another particular embodiment, X is CR$_6$R$_{6'}$ wherein R$_6$ and R$_{6'}$ are both H.

R$_1$ is H, —OR$_7$, an amino acid or —NR$_7$R$_{7'}$ wherein R$_7$ and R$_{7'}$ are independently H or a hydrocarbon chain, a carbocycle, a heterocycle, a carbocycle-substituted hydrocarbon chain or a heterocycle-substituted hydrocarbon chain optionally substituted with one or more hydroxyl, halogen (i.e. F, Cl, Br, I), cyano, amino (i.e. NH$_2$ or a secondary or tertiary amine), nitro, amidine (—C(NH)—NH$_2$), guanidine (—NH—C(NH)—NH$_2$), alkyl, halo-substituted alkyl, alkoxy, aryl or carboxyl. By "carboxyl" is meant herein as the free acid —COOH as well as esters thereof such as alkyl esters. By "alkoxy" is meant herein to include saturated, i.e. O-alkyl, and unsaturated, i.e. O-alkenyl and O-alkynyl, group. By "aryl" in meant herein to be an aromatic carbon ring or ring system such as benzene/phenyl, naphthyl, phenanthrenyl etc. as well as biphenyl. In a particular embodiment, R$_1$ is —OR$_7$ wherein R$_7$ is a hydrocarbon chain such as alkenyl i.e. allyl. In another embodiment R$_1$ is —NR$_7$R$_{7'}$ wherein R$_7$ is aryl or aralkyl optionally substituted with one or more hydroxyl, halogen, amino, amidine, guanidine, cyano, alkyl, alkoxy, halo-substituted alkyl; and R$_{7'}$ is H or alkyl. In a preferred embodiment, R$_1$ is —NR$_7$R$_{7'}$ wherein R$_7$ is phenyl or benzyl substitute with amidine or alkoxy and R$_{7'}$ is H or methyl. In a particularly preferred embodiment R$_7$ is benzyl, p-amidinylphenyl, p-methoxybenzyl or p-methylbenzyl and R$_{7'}$ is H.

In another embodiment, R$_1$ is —NR$_7$R$_{7'}$ wherein R$_7$ and R$_{7'}$ together form a heterocyle optionally fused to another heterocycle or carbocycle wherein said heterocycle and carbocycle are optionally substituted with one or more hydroxyl, halogen, amino, nitro, amidine, guanidine, alkyl, halo-substituted alkyl, alkoxy or carboxyl. In a particular embodiment, R$_7$ and R$_{7'}$ together form a piperidine ring fused to a benzene ring wherein said fused benzene ring is optionally substituted with one or more alkoxy. Preferably, the fused benzene ring is substituted at both beta carbon positions with methoxy.

$R_2$ is H or a hydrocarbon chain, a carbocycle or a carbocycle-substituted hydrocarbon chain optionally substituted with one or more hydroxyl, oxo (=O), halogen (preferably F or Cl), cyano, amino, nitro, amidine, guanidine, alkyl, halo-substituted alkyl, alkoxy (preferably methoxy) or carboxyl; and wherein said hydrocarbon chain is optionally interrupted with N, O, S, SO or $SO_2$. By "interrupted" is meant herein that one or more carbon atoms within a hydrocarbon chain is replaced with said heteroatom. When a hydrocarbon chain is interrupted with two or more heteroatoms, preferably the heteroatoms are non-adjacent. In the context of $R_2$, the heteroatom is adjacent to the ring nitrogen atom from which the hydrocarbon chain depends. In a preferred embodiment, $R_2$ is H, alkyl, cycloalkyl, aryl, cycloalkylalkyl or aralkyl optionally substituted with one or more alkyl, amino, amidine, guanidine or nitro. In a more preferred embodiment $R_2$ is H, alkyl, aryl, aralkyl or cycloalkyl and most preferably propyl, phenylethyl, cyclohexyl, o-nitrobenzyl or m-methylbenzyl.

$R_3$ is H or a protecting group. Preferably $R_3$ is H.

When 'n' is zero (0), $R_4$ is not present and X is attached to the benzamidine ring at that position. When n is the integer 1, $R_4$ is present and is selected from the group consisting of H, hydroxyl, halogen, amino, nitro, amidine, guanidine and acylamino. By "acylamino" is meant herein to be a carboxamide group —NHC(O)—hydrocarbon wherein the hydrocarbon is as previously defined and is preferably alkyl. Preferably, $R_4$ is H or amino and most preferably H.

$R_5$ is H or $R_4$ and $R_5$ together form a 5 or 6 member carbocycle or heterocycle ring optionally substituted with one or more hydroxyl, halogen, amino, nitro, amidine, guanidine or acylamino. In a particular embodiment, $R_5$ is H. In another particular embodiment, $R_4$ and $R_5$ form a benzene ring fused to the benzamidine ring from which $R_4$ and $R_5$ depend.

Preferred compounds of the invention include:

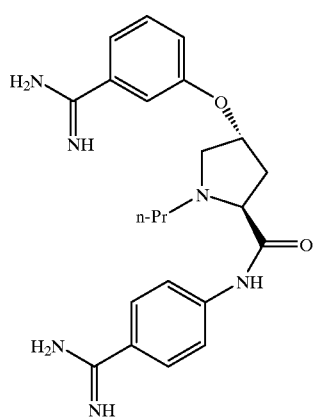

1

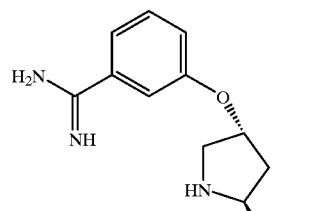

2

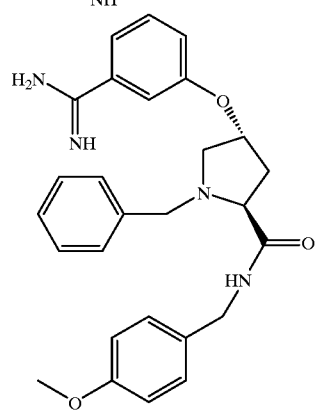

3

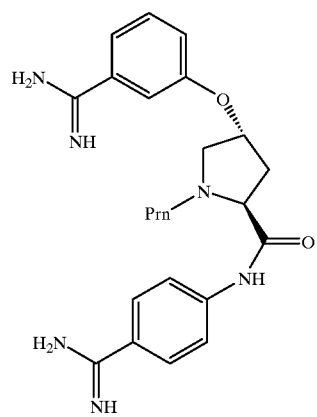

4

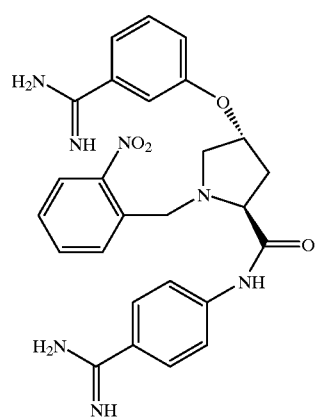

5

6
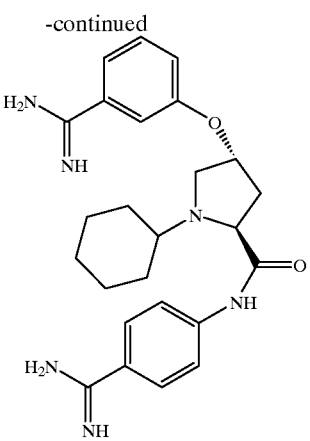
7
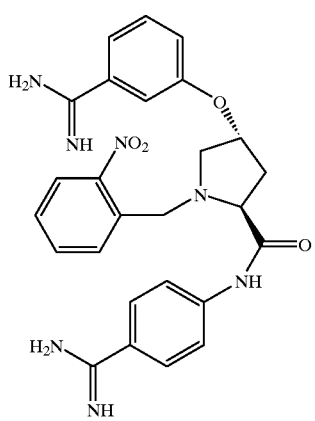
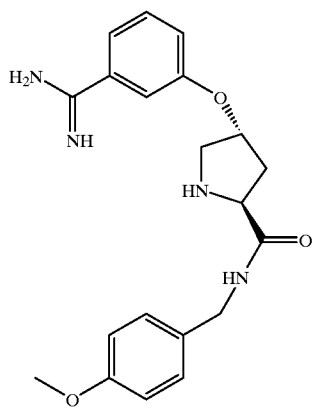
8
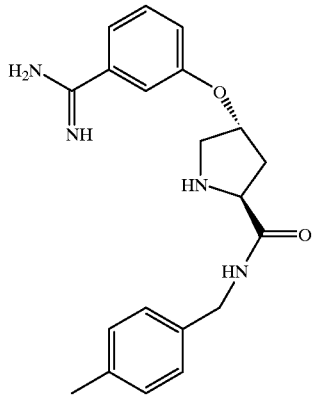
9
10
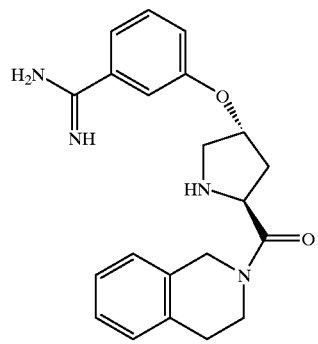
11
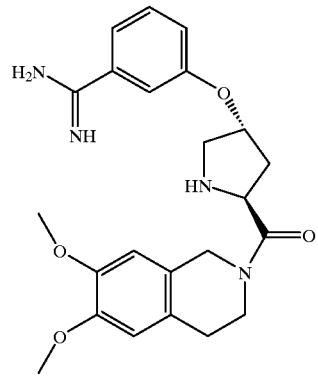
12
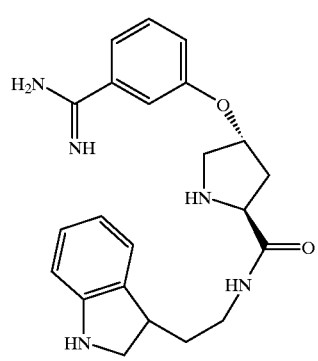
13
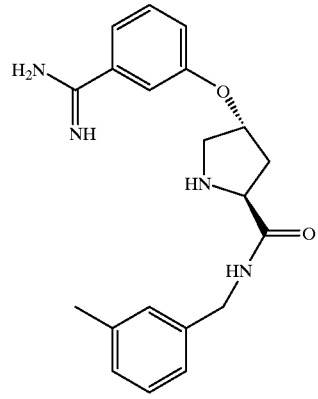

-continued
14
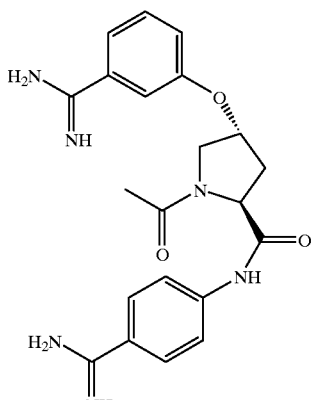
15
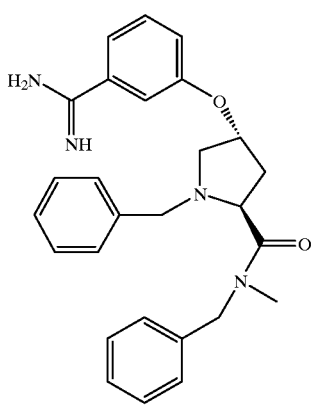
16
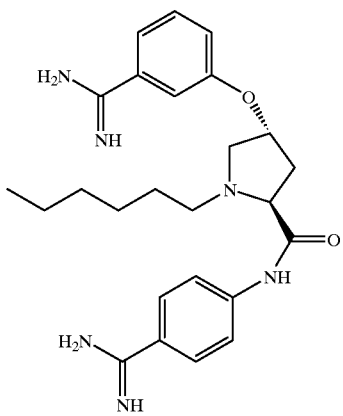
17
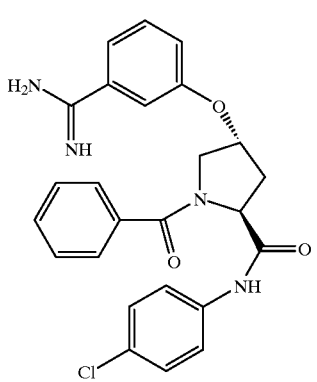
-continued
18
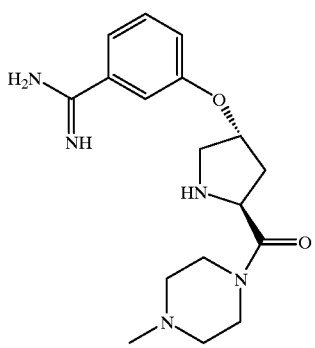
19
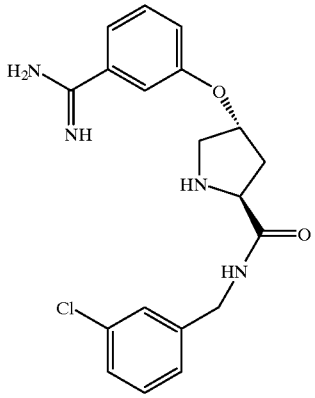
20
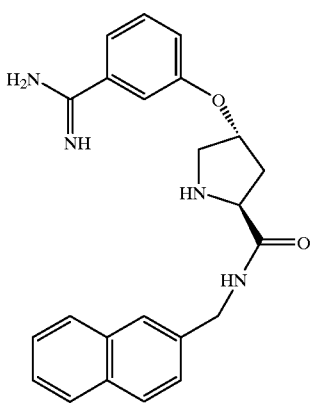
21
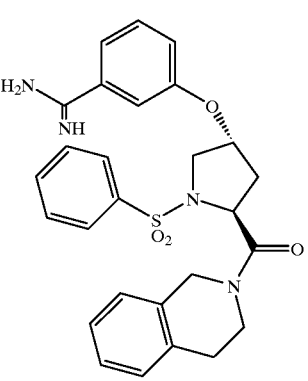

22
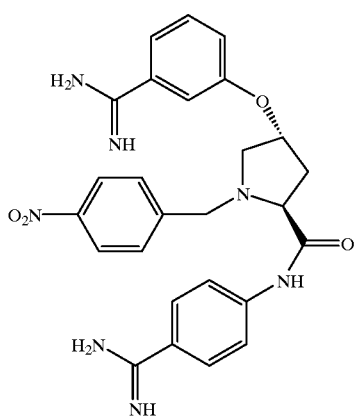
23
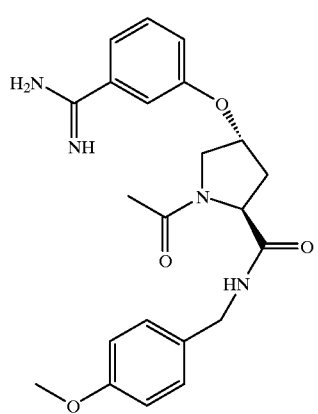
24
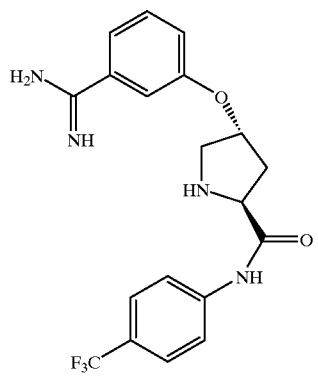
25
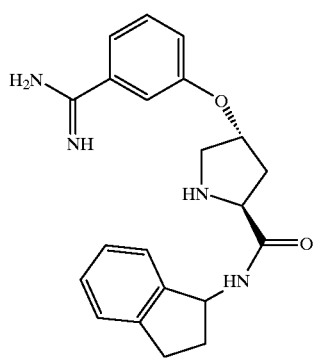
26
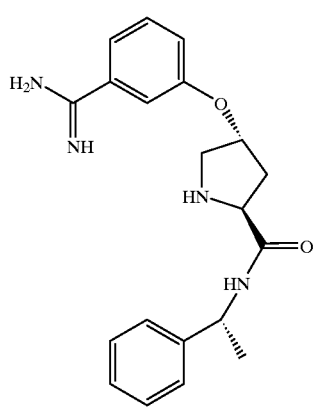
27
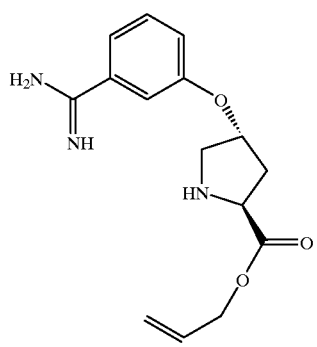
28
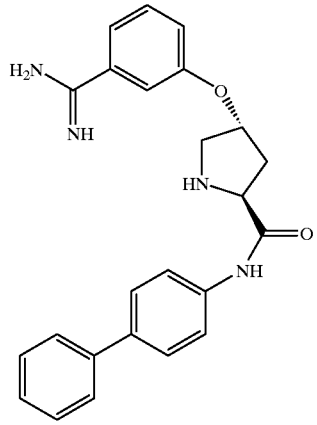
29
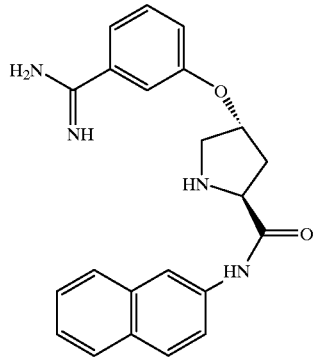

30
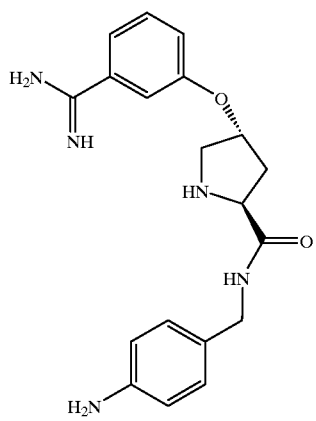
31
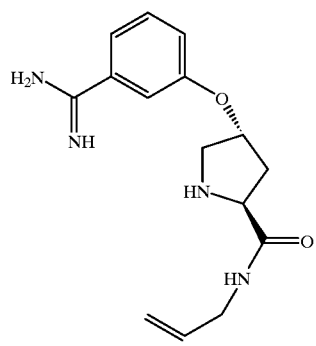
32
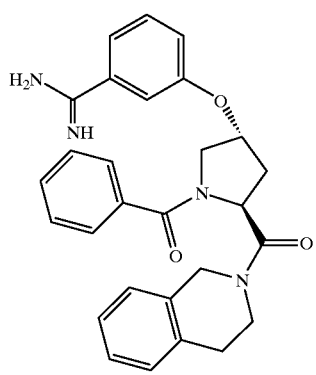
33
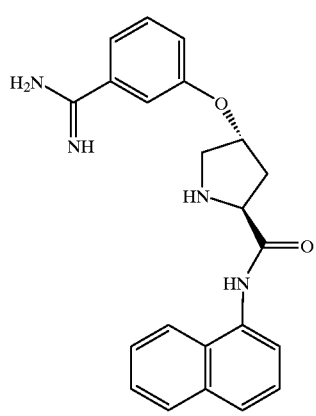
34
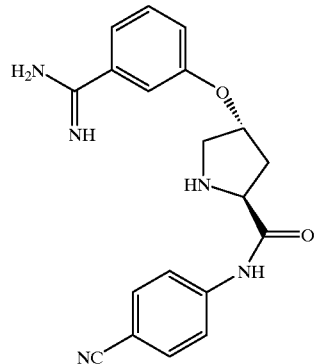
35
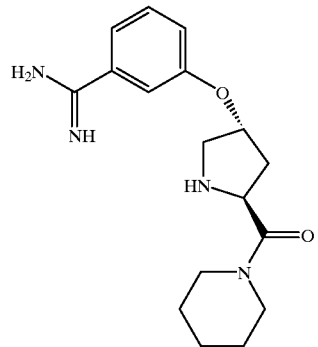
36
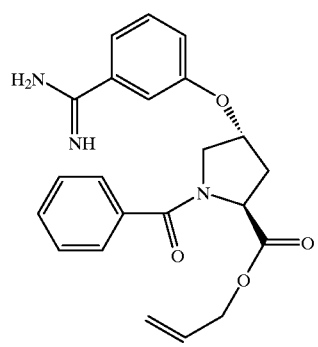
37
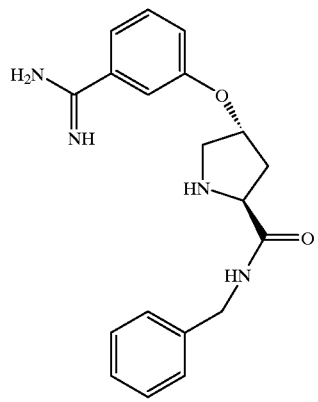

38
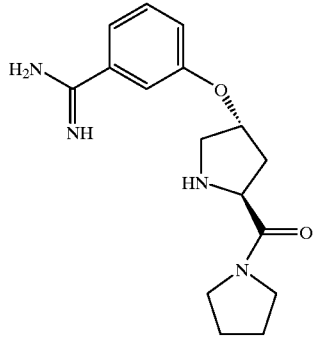
39
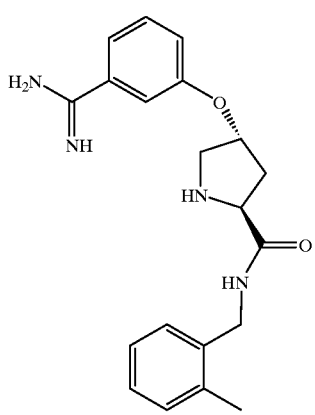
40
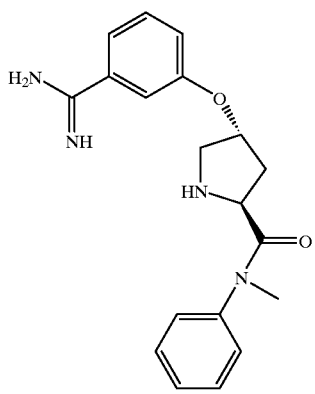
41
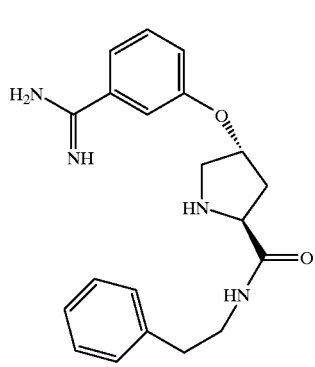
42
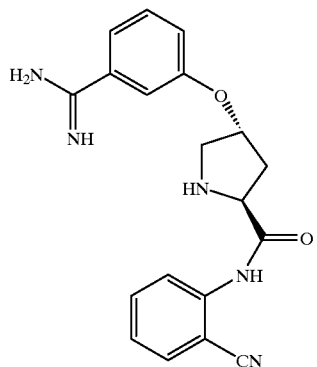
43
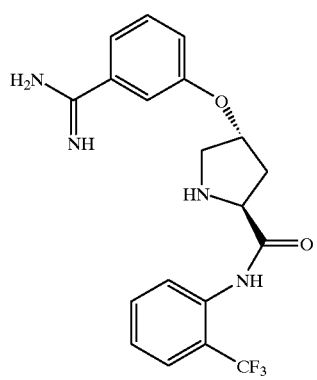
44
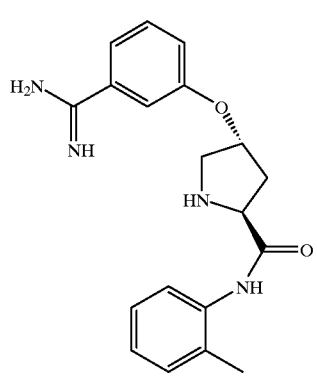
45
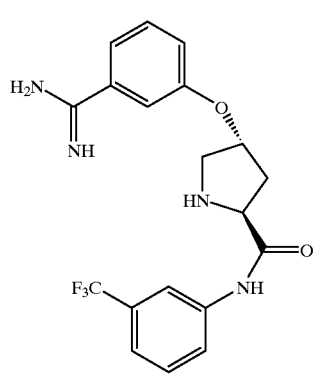

46
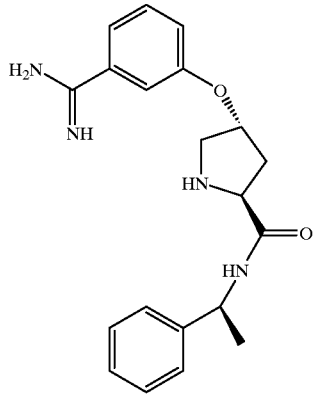
47
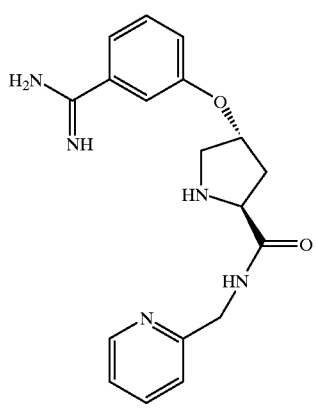
48
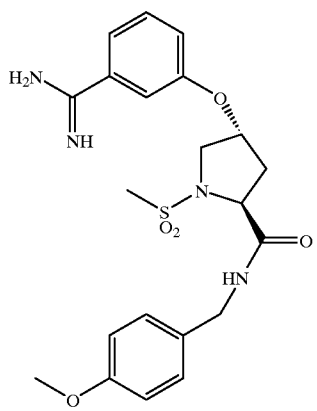
49
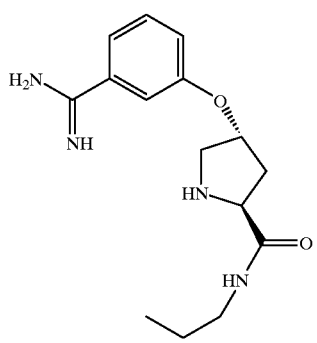
50
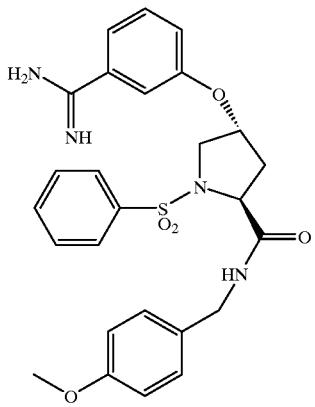
51
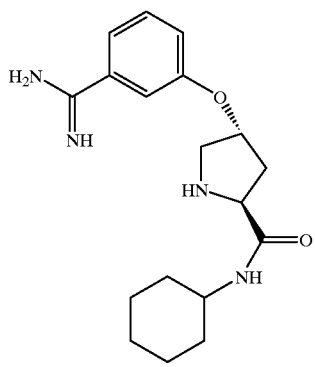
52
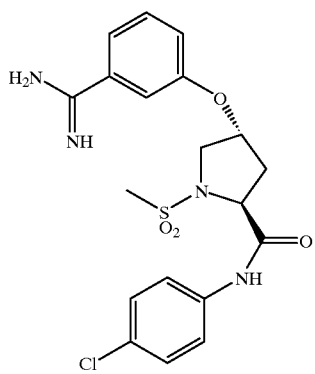
53
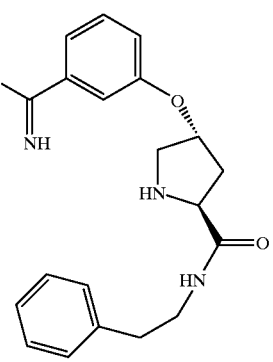

54
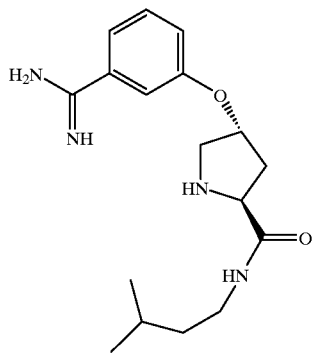
55
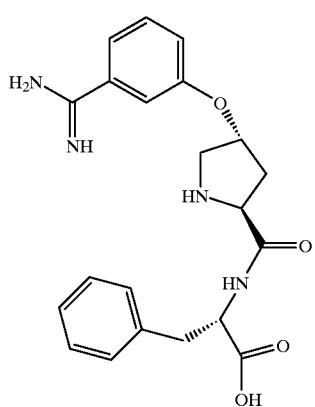
56
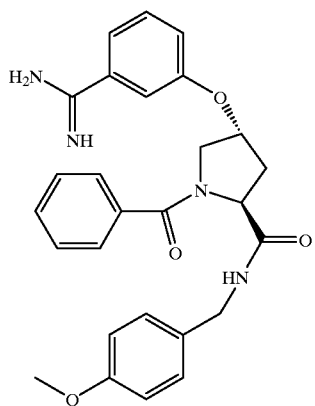
57
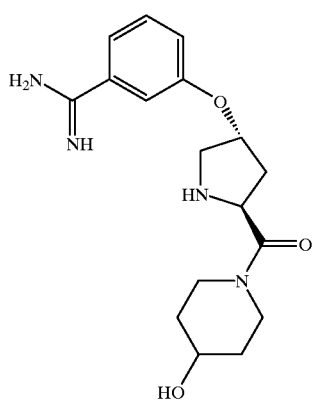
58
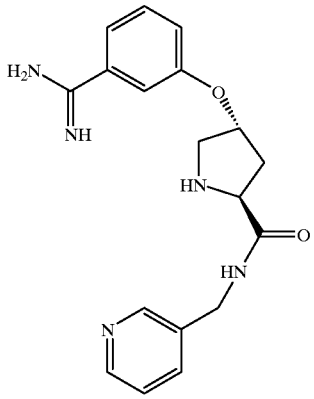
59
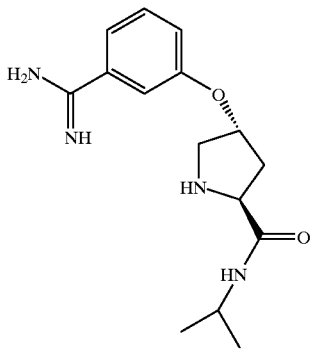
60
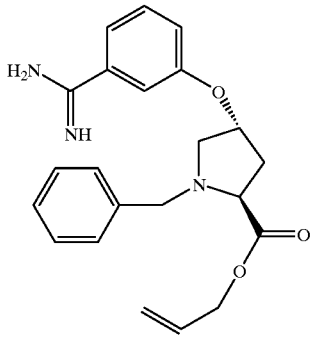
61
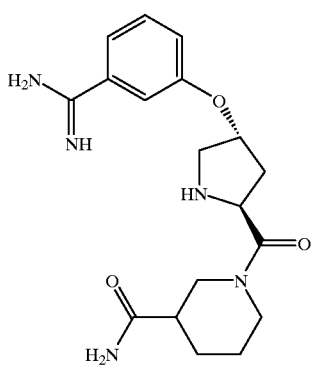

62
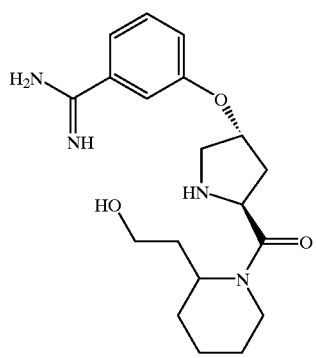
63
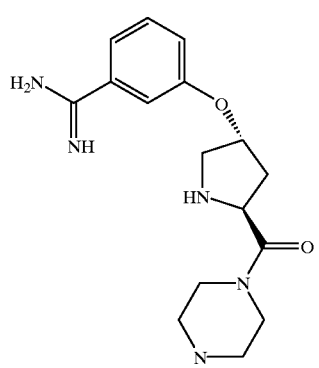
64
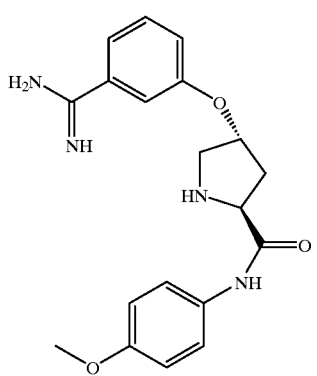
65
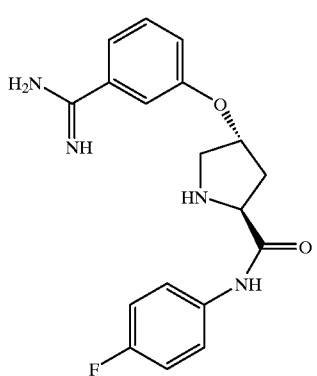
66
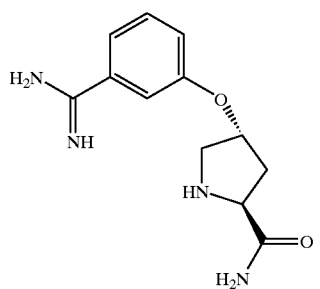
67
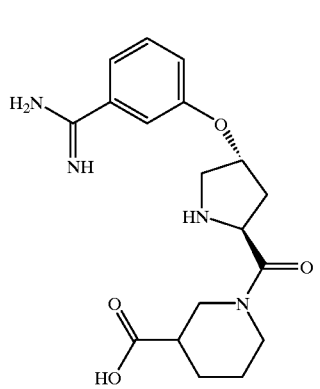
68
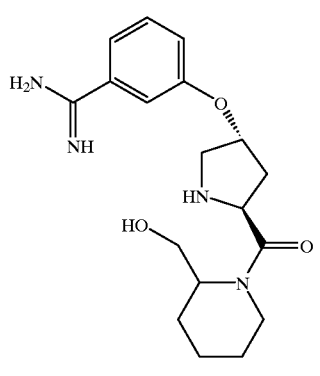
69
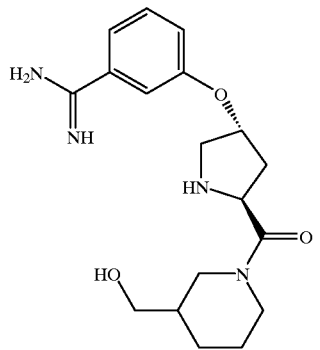

70
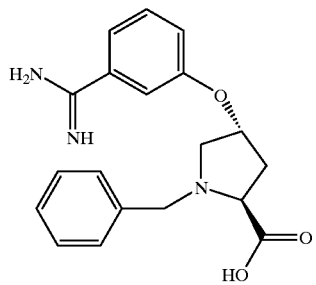
71
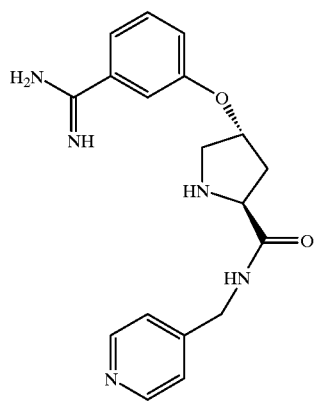
72
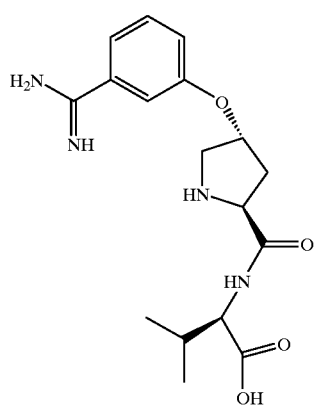
73
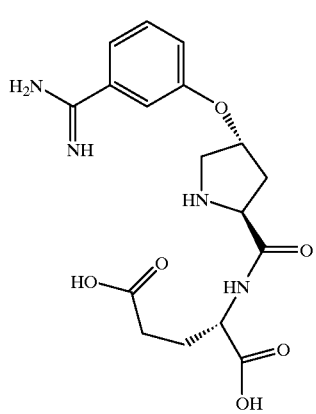
74
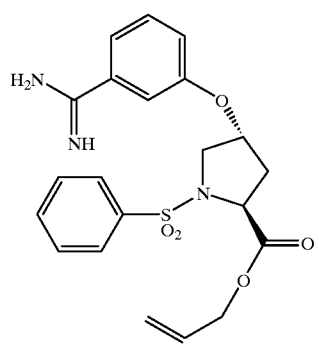
75
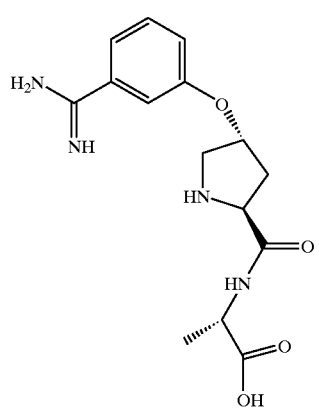
76
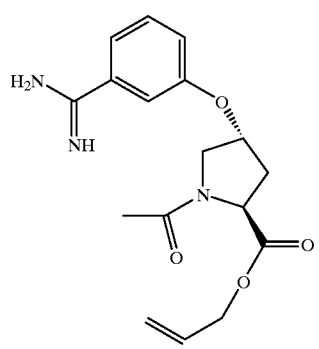
77
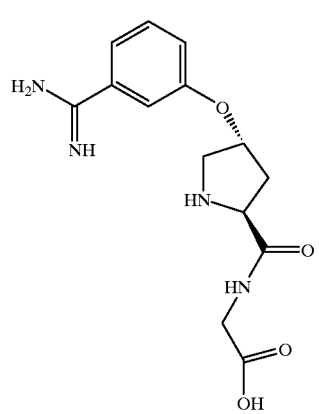

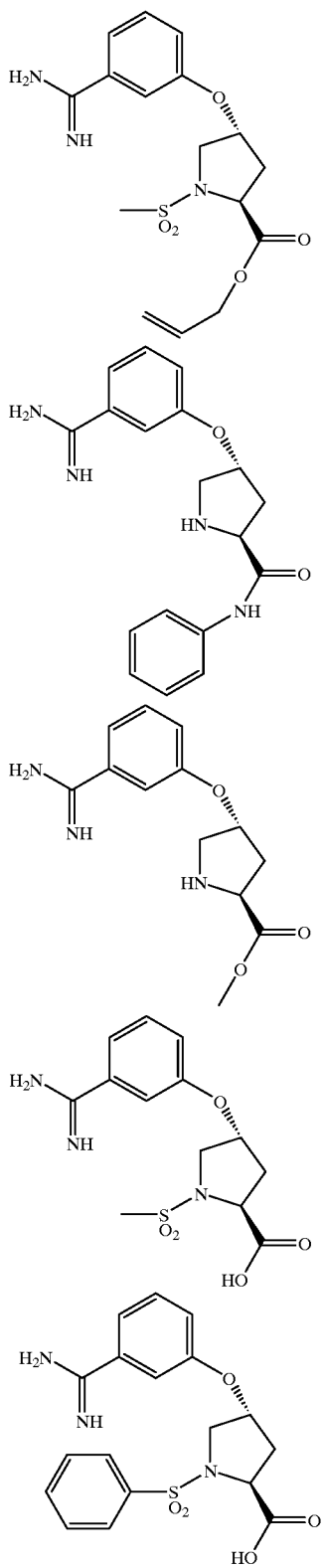

salts, solvates and hydrates thereof.

It will be appreciated that compounds of the invention may incorporate chiral centers and therefore exist as geometric and stereoisomers. All such isomers are contemplated and are within the scope of the invention whether in pure isomeric form or in mixtures of such isomers as well as racemates. Stereoisomeric compounds may be separated by established techniques in the art such as chromatography, i.e. chiral HPLC, or crystallization methods.

"Pharmaceutically acceptable" salts include both acid and base addition salts. Pharmaceutically acceptable acid addition salt refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, arylaliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, salicylic acid and the like.

Pharmaceutically acceptable base addition salts include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, trimethamine, dicyclohexylamine, choline, and caffeine.

Compounds of the invention may be prepared according to established organic synthesis techniques from starting materials and reagents that are commercially available or from starting materials that may be prepared from commercially available starting materials. Many standard chemical techniques and procedures are described in March, J., "Advanced Organic Chemistry" McGraw-Hill, New York, 1977; and Collman, J., "Principles and Applications of Organotransition Metal Chemistry" University Science, Mill Valley, 1987; and Larock, R., "Comprehensive Organic Transformations" Verlag, New York, 1989. It will be appreciated that depending on the particular substituents present on the compounds, suitable protection and deprotection procedures will be required in addition to those steps described herein. Numerous protecting groups are described in Greene and Wuts, Protective Groups in Organic Chemistry, 2d edition, John Wiley and Sons, 1991, as well as detailed protection and deprotection procedures. For example, suitable amino protecting groups include t-butyloxycarbonyl (Boc), fluorenyl-methyloxycarbonyl (Fmoc), 2-trimethylsilyl-ethyoxycarbonyl (Teoc), 1-methyl-1-(4-biphenylyl)ethoxycarbonyl (Bpoc), allyloxycarbonyl (Alloc), and benzyloxycarbonyl (Cbz). Carboxyl groups can be protected as fluorenylmethyl groups, or alkyl esters i.e. methyl or ethyl, or alkenyl esters such as allyl. Hydroxyl groups may be protected with trityl, monomethoxytrityl, dimethoxytrityl, and trimethoxytrityl groups.

In a particular embodiment wherein X is O, compounds of the invention may be prepared according to scheme 1.

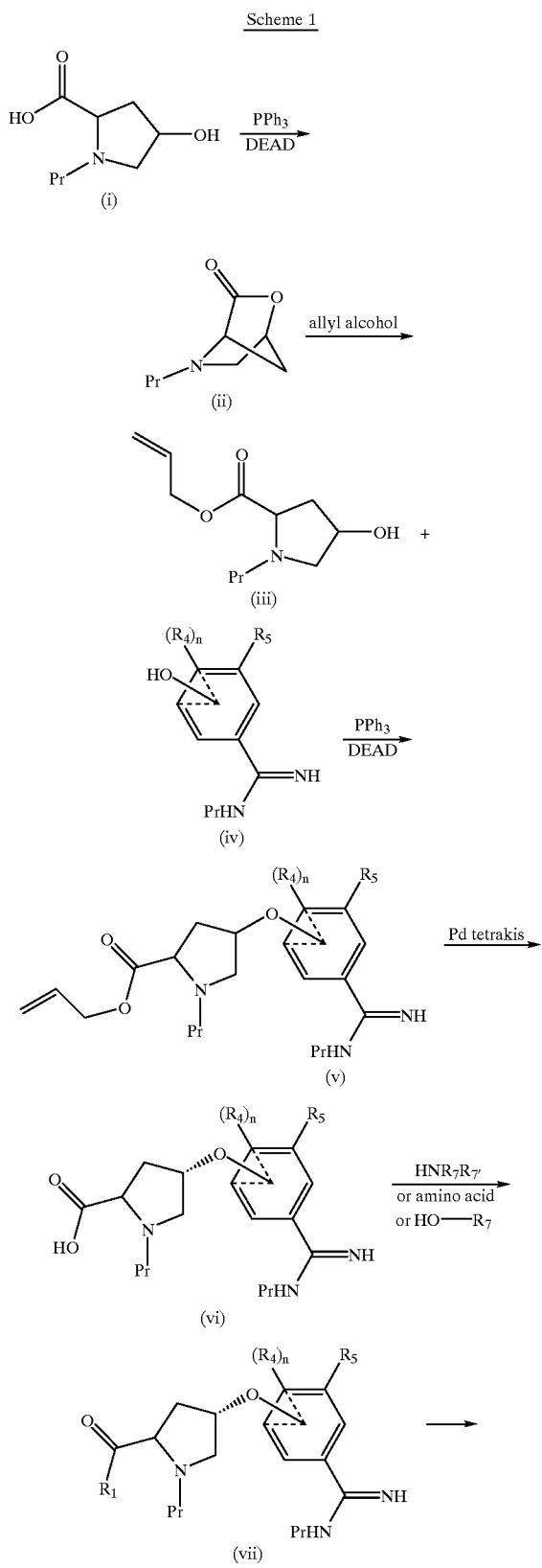

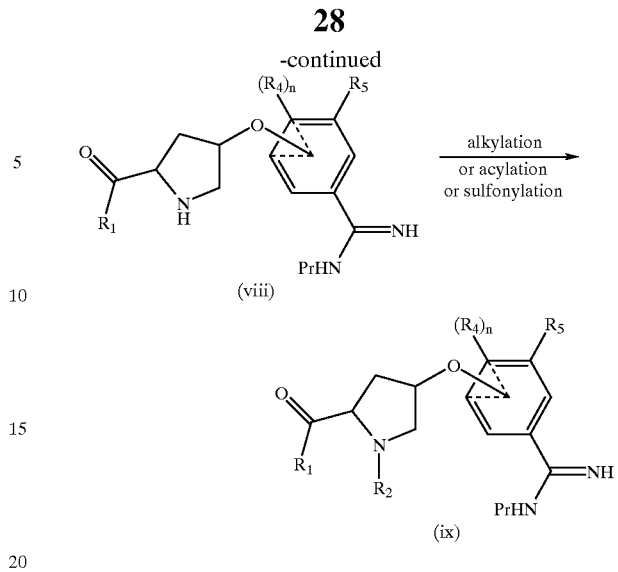

Referring to scheme 1, commercially available N-protected hydroxyproline (i.e. Boc or Teoc-protected) (i) is converted to allyl ester (iii) by reacting with triphenyl phosphine (PPh$_3$) and DEAD and then with allyl alcohol in the presence of Ti(IV)isopropoxide. The allyl ester (iii) is then coupled in a Mitsunobu reaction with N-protected meta- or para-hydroxybenzamidine (i.e. Boc-protected) in the presence of PPh$_3$ and DEAD to give intermediate (v). The allyl group is removed with Pd tetrakis (PPh$_3$) in an n-methyl morpholine (i.e. 5%), acetic acid (i.e. 2/5%) solution of chloroform to give free carboxylic acid (vi) which is reacted with amine HNR$_7$R$_{7'}$, an amino acid or alcohol HO—R$_7$ to give (vii). For amine HNR$_7$R$_{7'}$ and amino acid coupling, the carboxyl acid (vi) is first activated for example with HBTU and HOBt according to standard amide formation procedures. In a particular embodiment wherein R$_1$ of compounds of the invention is —NR$_6$-phenyl (optionally substituted), the carboxylic acid is activated with NCS and triphenyl phosphine followed by addition of anilines. The N-protecting group on the proline moiety is then removed from (vii) and the resulting compound (viii) is optionally alkylated acylated or sulfonylated to give compound (ix). When the protecting group is Teoc (trimethylsilylethoxycarbonyl), deprotection is achieved by treatment with tbaf (i.e. about 0.24M) in tetrahydrofuran (thf). Alkylation of intermediate (viii) is achieved via standard reductive amination using various aldehydes, a catalyst and an appropriate reducing agent, or can be achieved by SN$_2$ type displacements by treating with an alkyl halide and standard non-nucleophilic base. Acylation of intermediate (viii) is achieved by standard amide bond formation chemistry by activating the desired R$_2$ carboxylic acid and reacting with the free amine of (viii). Alternatively the amine of (viii) may be acylated by treating with various acid chlorides of R$_2$ and standard non-nucleophilic base such as Hunig's base. Sulfonylation of is achieved by reacting the free amine of intermediate (viii) with various sulfonyl chlorides of R$_2$ with a non-nucleophilic base such as a Hunig's base.

The amidine protecting group of (ix) is subsequently removed to give final compound of formula (I) of the invention wherein X is O.

In another particular embodiment wherein X is NH, compounds of the invention may be prepared according to scheme 2.

Scheme 2

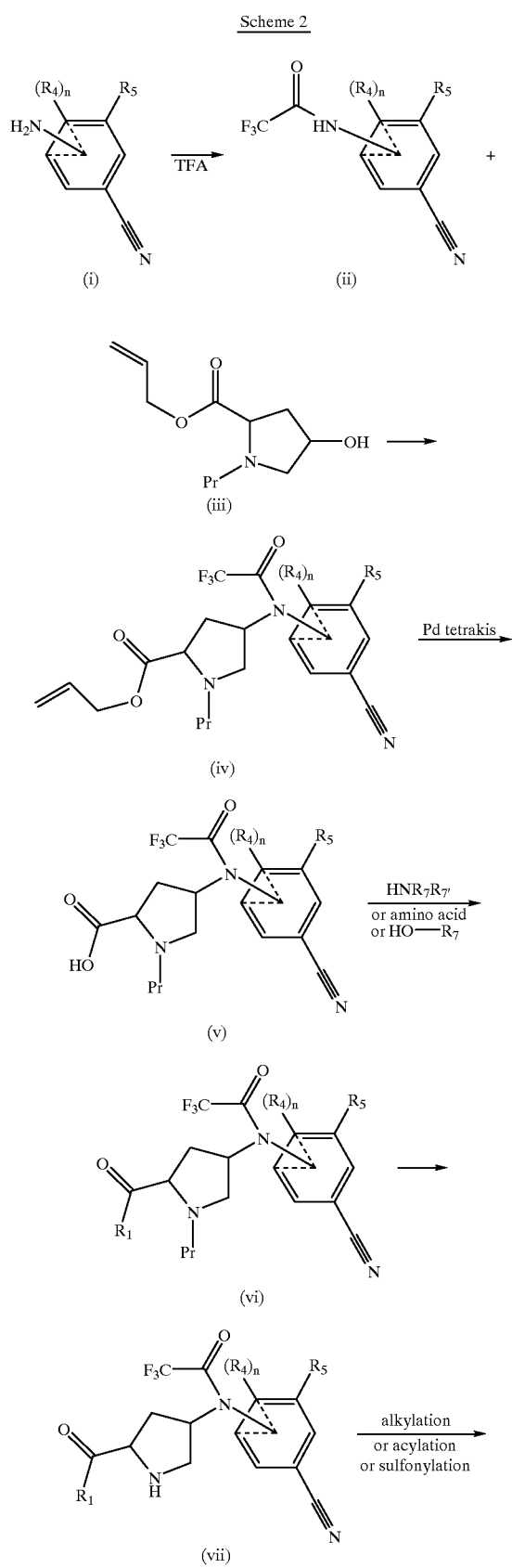

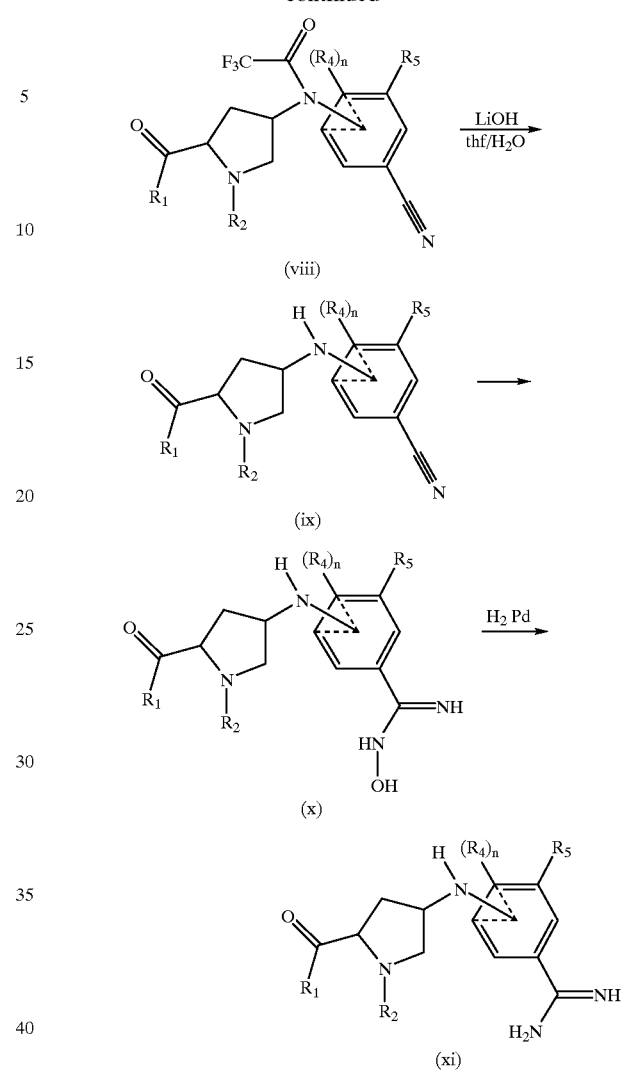

Referring to scheme 2, starting reagent cyanoaniline (i) is reacted with trifluoroacetic acid (TFA) activated with HBTU and HOBt to give intermediate (ii) which is coupled with allyl ester of N-protected hydroxyproline (iii) to give intermediate (iv). The allyl group is converted to the free carboxylic acid and then reacted with amine $HNR_7R_{7'}$, amino acid, or alcohol $HO-R_7$ and the N-protecting group on the proline is removed and optionally alkylated, acylated or sulfonylated as described with respect to scheme 1. The trifluoroacetyl group is removed by reacting (viii) with lithiumhydroxide in $thf/H_2O$ to give (ix). Nitrile intermediate (ix) is converted to a hydroxyamidine (x) by reacting with hydroxylamine hydrochloride and TEA and is subsequently reduced to amidine (xi) by treating with hydrogen and a metal hydrogenation catalysts such as Raney nickel or palladium.

In another particular embodiment wherein X is $CH_2$, compounds of the invention may be prepared according to scheme 3.

Scheme 3

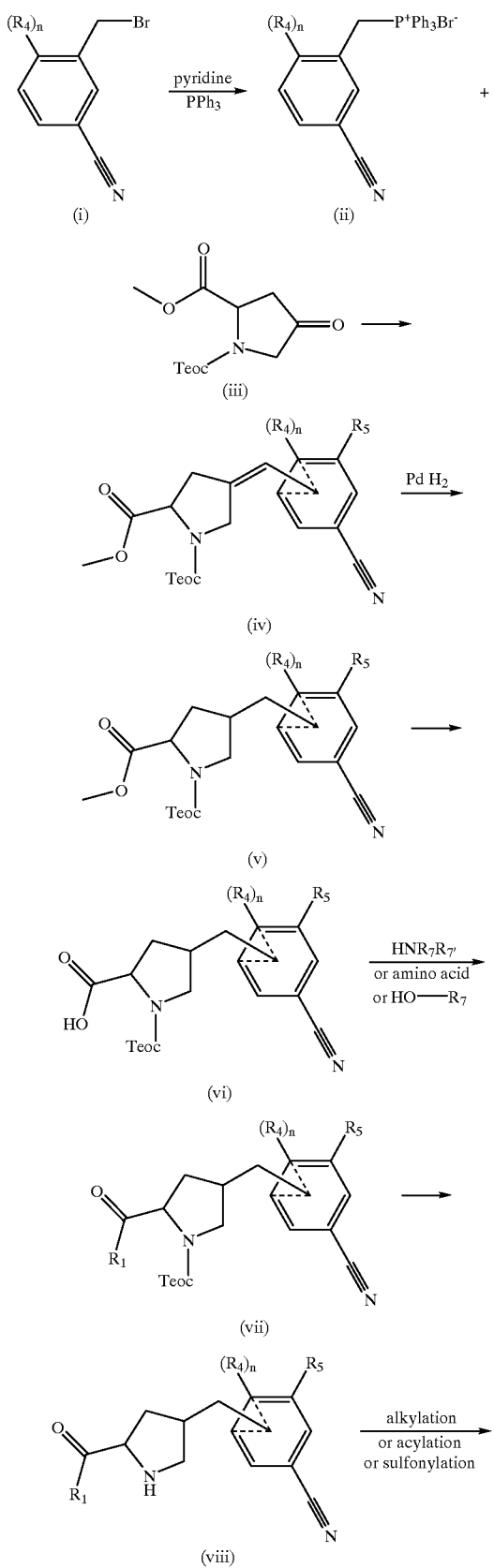

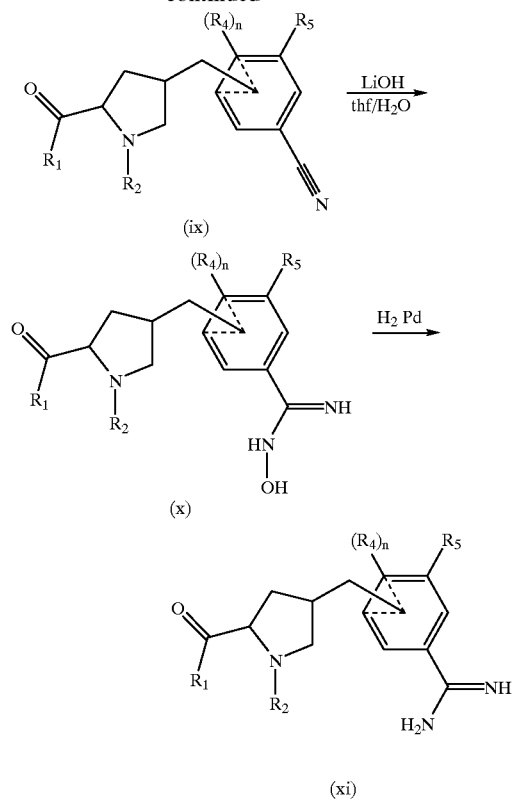

Referring to scheme 3, starting cyanobenzylbromide compound (i) is converted to a phosphonium salt (ii) by reacting with $PPh_3$ in pyridine which then undergoes a Wittig olefin forming reaction with keto-proline intermediate (iii) to give intermediate (iv). Intermediate (iii) is prepared from an N-protected proline ester for example N-Teoc protected proline methyl ester which undergoes a Swern oxidation in the presence of oxalochloride and triethylamine (TEA). Olefin intermediate (iv) is reduced with Pd catalyst and $H_2$ to give (v). The ester group is converted to the free carboxylic acid and then reacted with amine $HNR_7R_{7'}$, amino acid, or alcohol $HO-R_7$ and the N-protecting group on the proline is removed and optionally alkylated, acylated or sulfonylated as described with respect to scheme 1. Nitrile intermediate (ix) is converted to a hydroxyamidine (x) by reacting with hydroxylamine hydrochloride and TEA and is subsequently reduced to amidine (xi) by treating with hydrogen and a metal hydrogenation catalysts such as Raney nickel or palladium.

In an aspect of the invention, there is provided a method of inhibiting the binding of a serine protease (such as factor VIIa, TF/factor Xa complex, thrombin, trypsin, plasmin and kallikrein) to a protein ligand, the method comprising contacting said serine protease with a compound of formula (I). The method may be carried out in vivo or ex vivo as a solution based or cell based assay wherein the compound of the invention is introduced to the serine protease in the presence of a putative or known ligand of the protease. The compound of the invention may be labeled, for example isotopically radiolabeled, or labeled with a fluorophore such as FITC, to facilitate detection of ligand binding or reduction thereof to the protease. Thus compounds of the invention are useful for diagnostic and screening assays.

Compounds of the invention are therapeutically and/or prophylactically useful for treating diseases or conditions mediated by serine protease activity. Accordingly in an aspect of the invention, there is provided a method of treating a disease or condition mediated by serine proteases in a mammal, i.e. a human, comprising administering to said mammal an effective amount of a compound of the invention. By "effective amount" is meant an amount of compound which upon administration is capable of reducing the activity of the serine protease; or the amount of compound required to prevent, inhibit or reduce blood coagulation or thrombus formation upon administration; or is capable of alleviating or reducing the severity of symptoms associated with the disease or condition mediated by serine proteases. Compounds of the invention may also be used as an additive to blood samples or reserves in order to prevent coagulation. Accordingly there is also provided a method of inhibiting coagulation of mammalian blood (i.e. human blood), comprising introducing a compound of the invention to said blood.

The actual amount of compound administered and the route of administration will depend upon the particular disease or condition as well as other factors such as the size, age, sex and ethnic origin of the individual being treated and is determined by routine analysis. In general, intravenous doses will be in the range from about 0.01–1000 mg/kg of patient body weight per day, preferably 0.1 to 20 mg/kg and 0.3 to 15 mg/kg. Administration may be once or multiple times per day for several days, weeks or years or may be a few times per week for several weeks or years. The amount of compound administer by other routes will be that which provides a similar amount of compound in plasma compared to the intravenous amounts described which will take into consideration the plasma bioavailability of the particular compound administered.

In methods of the invention, the compound may be administered orally (including buccal, sublingual, inhalation), nasally, rectally, vaginally, intravenously (including intrarterially), intradermally, subcutaneously, intramuscularly and topically. Compounds will be formulated into compositions suitable for administration for example with suitable carriers, diluents, thickeners, adjuvants etc. as are routine in the formulation art. Accordingly, another aspect of the invention provides pharmaceutical compositions comprising a compound of formula (I) and a pharmaceutically acceptable carrier, excipient or adjuvant.

Compositions of the invention may also include additional active ingredients in particular additional anticoagulants (eg. aspirin, warfarin, heparin) and/or thrombolytic agents (eg. streptokinase, tPA, TNKase™). Dosage forms include solutions, powders, tablets, capsules, gel capsules, suppositories, topical ointments and creams and aerosols for inhalation. Formulations for non-parenteral administration may include sterile aqueous solutions which may also contain buffers, diluents and other suitable additives. Pharmaceutically acceptable organic or inorganic carrier substances suitable for non-parenteral administration which do not deleteriously react with compounds of the invention can be used. Suitable pharmaceutically acceptable carriers include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like. The formulations can be sterilized and, if desired, mixed with auxiliary agents, e.g., lubricants, preservatives, stabilizers, wetting agents, emulsifiers, salts for influencing osmotic pressure, buffers, colorings flavorings and/or aromatic substances and the like which do not deleteriously react with compounds of the invention. Aqueous suspensions may contain substances which increase the viscosity of the suspension including, for example, sodium carboxymethylcellulose, sorbitol and/or dextran. Optionally, the suspension may also contain stabilizers.

In a preferred embodiment, compounds of the invention are administered via oral delivery. Compositions for oral administration include powders or granules, suspensions or solutions in water or non-aqueous media, capsules, sachets, troches, tablets or SECs (soft elastic capsules or caplets). Thickeners, flavoring agents, diluents, emulsifiers, dispersing aids, carrier substances or binders may be desirably added to such formulations. Such formulations may be used to effect delivering the compounds to the alimentary canal for exposure to the mucosa thereof. Accordingly, the formulation can consist of material effective in protecting the compound from pH extremes of the stomach, or in releasing the compound over time, to optimize the delivery thereof to a particular mucosal site. Enteric coatings for acid-resistant tablets, capsules and caplets are known in the art and typically include acetate phthalate, propylene glycol and sorbitan monoleate.

Various methods for producing formulations for alimentary delivery are well known in the art. See, generally *Remington's Pharmaceutical Sciences*, 18th Ed., Gennaro, ed., Mack Publishing Co., Easton, Pa., 1990. The formulations of the invention can be converted in a known manner into the customary formulations, such as tablets, coated tablets, pills, granules, aerosols, syrups, emulsions, suspensions and solutions, using inert, non-toxic, pharmaceutically suitable excipients or solvents. The therapeutically active compound should in each case be present in a concentration of about 0.5% to about 99% by weight of the total mixture, that is to say in amounts which are sufficient to achieve the desired dosage range. The formulations are prepared, for example, by extending the active compounds with solvents and/or excipients, if appropriate using emulsifying agents and/or dispersing agents, and, for example, in the case where water is used as the diluent, organic solvents can be used as auxiliary solvents if appropriate.

Compositions may also be formulated with binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrates (e.g., starch or sodium starch glycolate); or wetting agents (e.g., sodium lauryl sulfate). Tablets may be coated by methods well known in the art. The preparations may also contain flavoring, coloring and/or sweetening agents as appropriate.

Formulations of the present invention suitable for oral administration may be presented as discrete units such as capsules, cachets or tablets each containing predetermined amounts of the active ingredients; as powders or granules; as solutions or suspensions in an aqueous liquid or a non-aqueous liquid; or as oil-in-water emulsions or water-in-oil liquid emulsions. A tablet may be made by compression or molding, optionally with one or more accessory ingredients. Compressed tablets may be prepared by compressing in a suitable machine, the active ingredients in a free-flowing form such as a powder or granules, optionally mixed with a binder, lubricant, inert diluent, preservative, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredients therein.

EXAMPLE 1

Synthesis of Benzamidine Compounds

Step 1

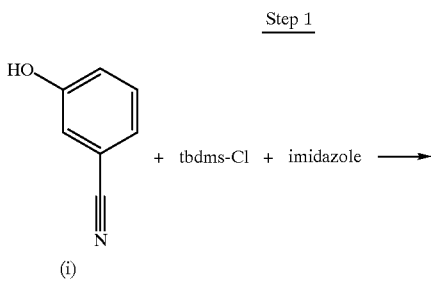

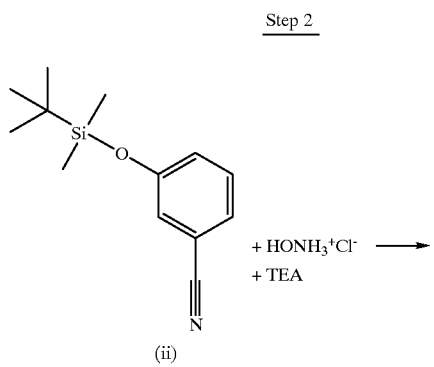

10 g (84 mmol) of 3-hydroxy benzonitrile and 17.2 g (252 mmol) of imidazole were dissolved in 300 ml of dmf. To this solution, 38.0 g (252 mmol) of t-butyldimethylsilylchloride (tbdms-Cl) was added and the reaction was agitated at room temperature for 12 h. The dimethylformamide was removed by concentration in vacuo and redissolved in a copious amount of ethyl acetate. The organic layer was then washed with water twice, and with brine twice. The organic layer was then dried over magnesium sulfate and concentrated in vacuo. The crude mixture was then purified by flash chromatography using an ether solvent system to afford 18.6 g (95% yields) of (ii).

Step 2

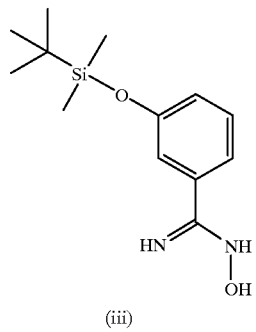

12 g (51.2 mmol) of (ii) was dissolved in 150 ml of ethanol. To this solution, 18.0 g (255 mmol) of hydroxylamine hydrochloride and 45.0 ml (255 mmol) of triethylamine were added and the reaction was stirred at 60° C. overnight. The reaction was concentrated in vacuo, redissolved in ethyl acetate and washed with water and brine. The organic layer was dried over magnesium sulfate and concentrated in vacuo to yield 12.0 g (88% yield) of crude material.

Step 3

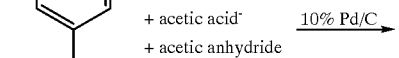

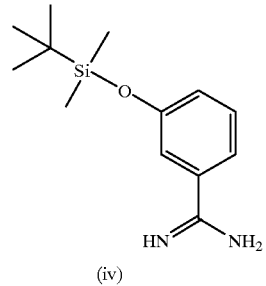

12.0 g (42 mmol) of crude (iii) was dissolved in 200 ml of ethanol. To this solution was added 3.6 ml (60 mmol) of acetic acid and 6.0 ml of acetic anhydride. 2.0 g of 10% palladium on carbon was then added to the reaction. Subsequently, the reaction was placed under hydrogen and stirred at room temperature overnight. The reaction was filtered through celite, concentrated in vacuo, and azeotroped with benzene twice to afford 11.7 g (90% yield) of (iv).

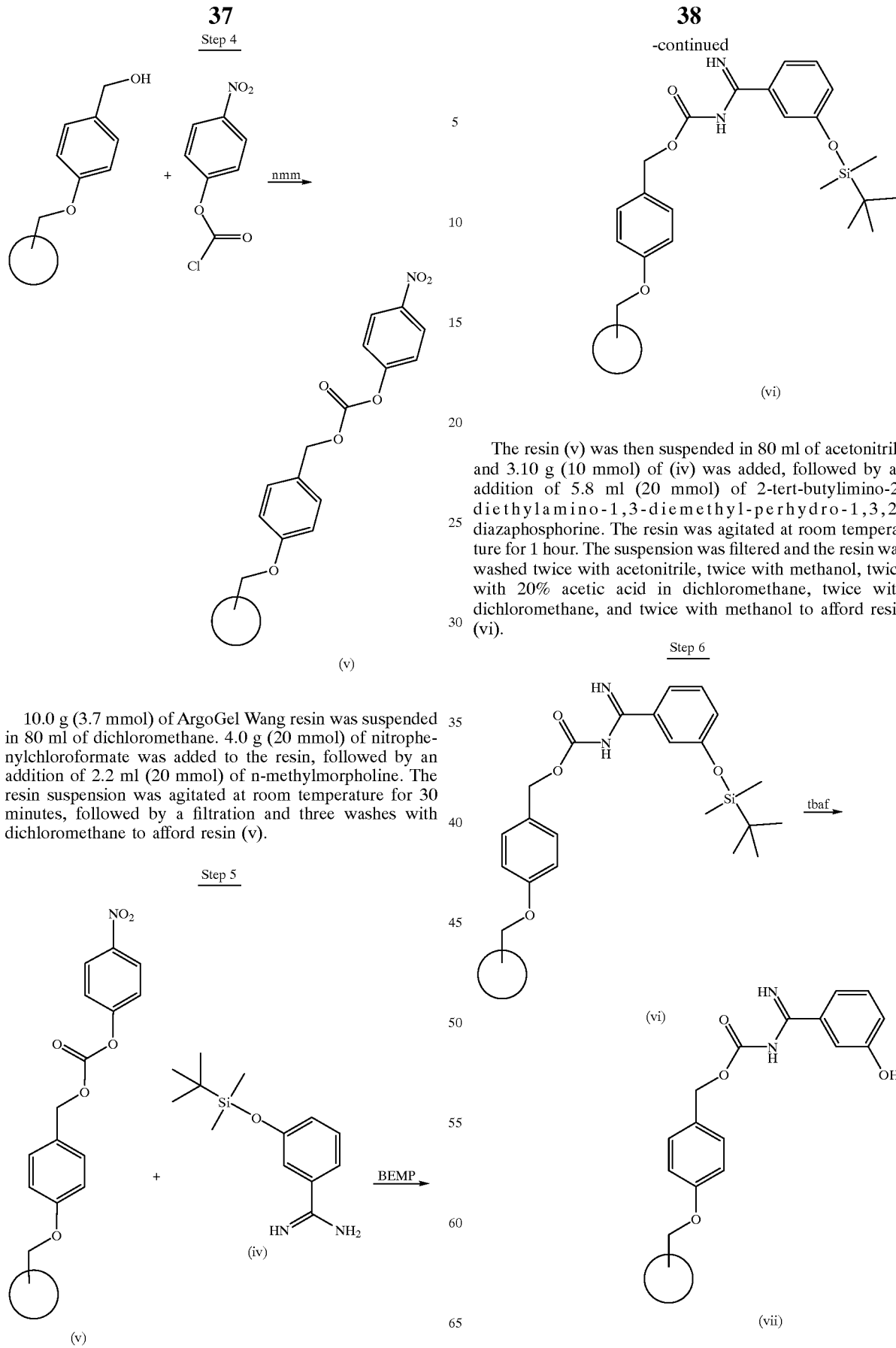

10.0 g (3.7 mmol) of ArgoGel Wang resin was suspended in 80 ml of dichloromethane. 4.0 g (20 mmol) of nitrophenylchloroformate was added to the resin, followed by an addition of 2.2 ml (20 mmol) of n-methylmorpholine. The resin suspension was agitated at room temperature for 30 minutes, followed by a filtration and three washes with dichloromethane to afford resin (v).

The resin (v) was then suspended in 80 ml of acetonitrile and 3.10 g (10 mmol) of (iv) was added, followed by an addition of 5.8 ml (20 mmol) of 2-tert-butylimino-2-diethylamino-1,3-diemethyl-perhydro-1,3,2-diazaphosphorine. The resin was agitated at room temperature for 1 hour. The suspension was filtered and the resin was washed twice with acetonitrile, twice with methanol, twice with 20% acetic acid in dichloromethane, twice with dichloromethane, and twice with methanol to afford resin (vi).

Resin (vi) was suspended in 80 ml of a 0.25 M tbaf solution in thf for 30 minutes. The suspension was then filtered, washed three times with tetrahydrofuran, two times with 20% acetic acid in dichloromethane, two times with methanol, and two times with dichloromethane to afford (vii).

Step 7

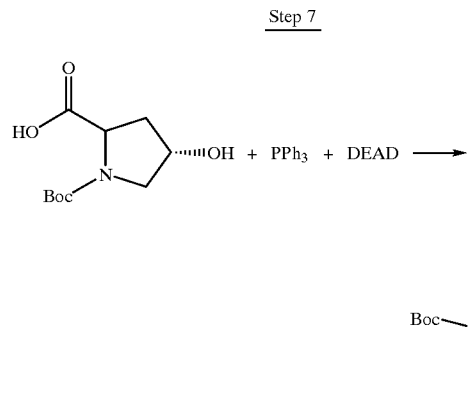

Dissolved 10.0 g (43.2 mmol) of N-Boc-trans-L-hydroxyproline in 400 ml of tetrahydrofuran. Added 14.7 g (56.2 mmol) of triphenylphosphine and cooled the reaction to 0° C. and added 8.9 ml (56.2 mmol) of DEAD dropwise over 5 minutes using an addition funnel. Let go for 30 minutes at 0° C., followed by a removal of thf by concentration under vacuum. Redilutred in ether and stored at 4° C. overnight to recrystallize out the triphenylphosphine oxide by-product. Filtered the recrystallization and washed the crystals two times with ether. Added hexane until filtrate turned cloudy and stored at 4° C. overnight to recrystallize out product. Collected the crystals by filtration and washed the crystals twice with cold hexanes. This afforded 6.4 g (70% yield) of (viii).

Step 8

6.4 g (30 mmol) of (viii) was dissolved in 100 ml of allyl alcohol and the reaction was cooled to 0° C. 144 mg (6.0 mmol) of Sodium Hydride was added and the reaction was warmed to room temperature by removal of the ice bath. Upon reaching room temperature, the reaction was quenched with an addition of 3.6 ml (60 mmol) of acetic acid. The reaction was then diluted with 900 ml of ethyl acetate and washed two times with water and twice with brine. The organic was then dried over magnesium sulfate and concentrated in vacuo. The crude mixture was then purified through a silica plug using a 1:1 ether/ethyl acetate to afford 6.5 g (24 mmol, 80% yield) of (ix) as an oil.

Step 9

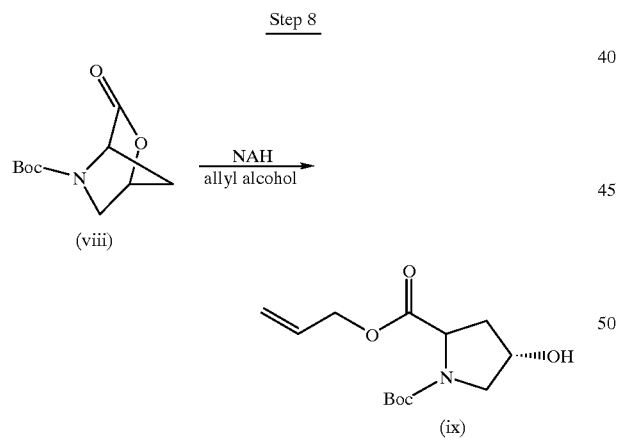

4.0 g (15.3 mmol) of (ix) was dissolved in 80 ml of a 1:1 mixture of thf and dcm. To this solution, 10.0 g (3.5 mmol) of resin (vi) was added and the reaction was cooled to 0° C. with an ice bath. 4.0 g (15.3 mmol) of triphenylphosphine was added, followed by a dropwise addition of 2.4 ml (15.3 mmol) of diethylazidodicarboxylate. The reaction was then allowed to warm to room temperature and stirred overnight. This was followed by a filtration. The resin was then washed twice with tetrahydrofuran, twice with 20% acetic acid in dichloromethane, twice with methanol, and twice with dichloromethane to afford resin (x)

Step 10

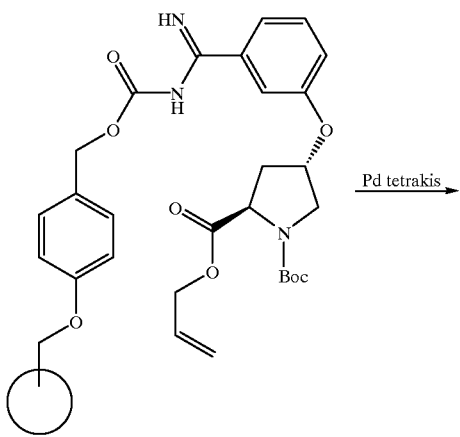

(x)

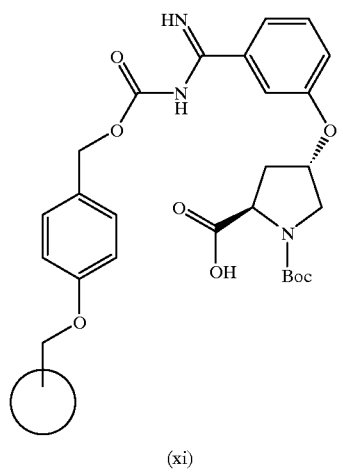

(xi)

11.0 g (3.5 mmol) of resin (x) was suspended in 80 ml of 5% acetic acid and 2.5% n-methylaniline in dichloromethane. 3.2 g (2.8 mmol) of tetrakis(triphenylphosphine)palladium(0) was then added and the reaction suspension was agitated for 30 minutes. Following filtration, the resin was washed twice with 20% diisopropylethylamine(dipea) in dichloromethane, twice with dcm, twice with 20% acetic acid in dcm, twice with methanol, and twice with dcm to afford resin (xi).

Step 11 and 12

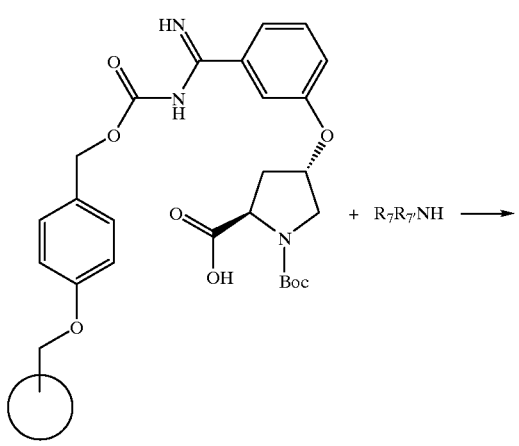

(xi)

-continued

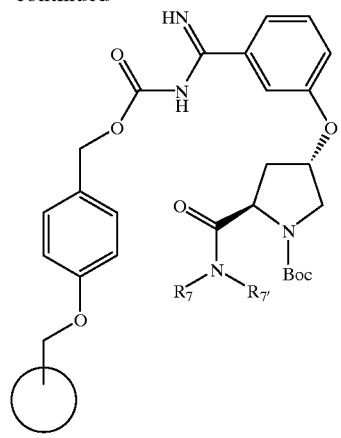

(xii)

Standard parallel amine addition to resin (11) was as follows; 100 mg (0.035 mmol) of resin (11) was loaded into a Quest RV equipped with a magnetic stir bar. 2.0 ml of a stock 0.6 M solution of HBTU and HOBt in dimethylacetamide(dma) was added to the resin and the suspension was agitated for 10 min. This was followed by an addition of 2.0 ml of a 0.6 M stock solution of dipea in dma. 5 minutes after the dipea addition, 1.2 mmol of the selected amine was added and the reaction was agitated for 30 minutes. The resin was then drained and washed twice with dma, twice with methanol, and twice with dichloromethane.

Standard parallel aniline addition to resin (xi) is as follows: Loaded 100 mg of resin (xii) into Quest RV: Added 2.0 ml of a 0.6 M stock solution of triphenylphosphine in dcm and cooled the reaction to 0° C. using Quest chiller. This was followed by an addition of 2.0 ml of a 0.6 M stock solution of N-chlorosuccinimide in acetonitrile and the reaction was agitated at 0° C. for 15 minutes. The reaction was then drained and washed three times with dichloromethane while cooling was maintained. 3.0 ml of 0.3 M solution of selected aniline in acetonitrile was then added and the reaction was then allowed to warm to RT by disengaging of Quest chiller. The reaction was then agitated at RT for 1 hour. After draining, the resin was washed three times with methanol, twice with 20% acetic acid in dcm, twice with methanol, and twice with dcm Step 13

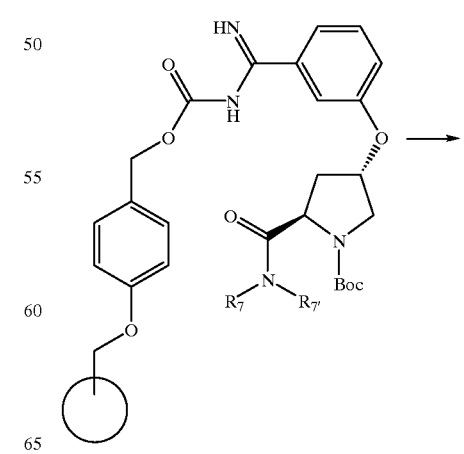

(xii)

-continued

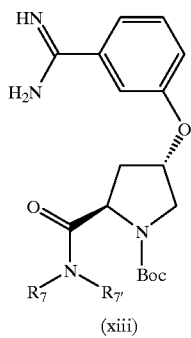

(xiii)

Compound cleavage and N-Boc cleavage of resins of type (xii) was carried out by incubation of the resin in 3.0 ml of straight trifluoroacetic acid. The tfa was drained into scintillation vials and washed one time with 3.0 ml of trifluoroacetic acid. The samples were then concentrated and purified by reverse phase HPLC to afford compounds of class (xiii). Typical purified yields ranged from 3.0 to 5.0 mg.

Step 14

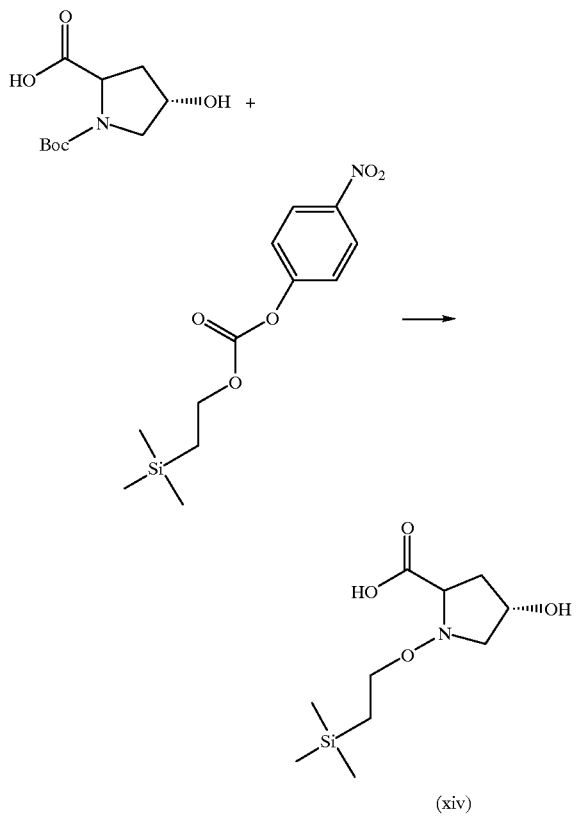

15.4 g (117.4 mmol) trans-L-hydroxyproline and 16.21 g (153 mmol) of Sodium Carbonate was dissolved in 250 ml of water. 43.3 g (153 mmol) of 2-(trimethylsilyl)ethyl p-nitrophenyl carbonate was dissolved in 250 ml of dioxane and this solution was dripped into the aforementioned aqueous solution over 10 min. The reaction was stirred at room temperature overnight. The reaction was then concentrated in vacuo and rediluted in a copius amount of ethyl acetate and 1.0 M citric acid. The organic was collected and the aqueous was extracted two times with ethyl acetate. The organics were combined, washed twice with water and twice with brine. The organic was then dried over magnesium sulfate and concentrated in vacuo. The crude mixture was then purified by flash chromatography to yield 32.3 g (60% yield) of (xiv)

Step 15

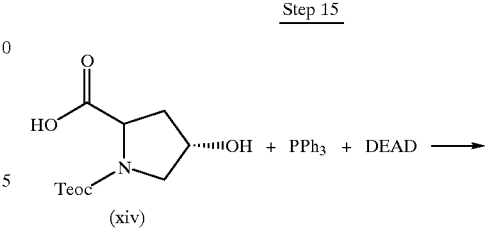

9.0 g (32.8 mmol) of (xiv) was dissolved in 340 ml of tetrahydrofuran and cooled to 0° C. 11.2 g (42.6 mmol) of triphenylphosphine was then added, followed by a dropwise addition of 6.7 ml (42.6 mmol) of DEAD over 5 minutes. The reaction was stirred at 0° C. for 30 minutes, followed by a vacuum concentration. The reaction was diluted with ether and washed twice with sat. sodium bicarbonate, twice with water, and twice with brine. The organic was dried over magnesium sulfate and purified by flash chromatography using 1:1 ether/hexane to afford 6.7 g (80% yield) of (xv).

Step 16

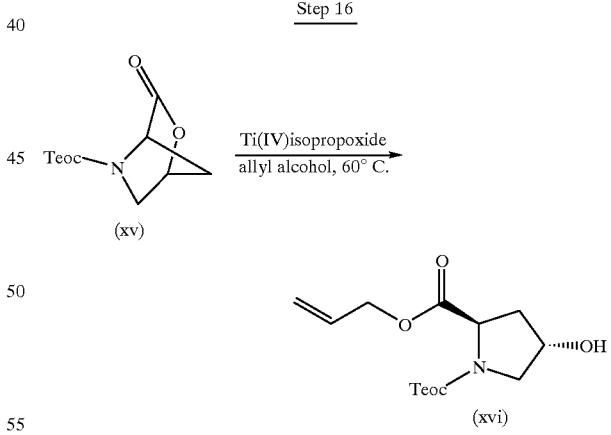

6.0 g (22.6 mmol) of (xv) was dissolved in 100 ml of allyl alcohol and to this solution was added 3.0 ml (10 mmol) of titanium isopropoxide. The reaction was heated to 60° C. and stirred overnight. The reaction was diluted with 900 ml of ethyl acetate and washed twice with saturated sodium bicarbonate, twice with water, and twice with brine. The organic was then dried over magnesium sulfate and concentrated in vacuo. The crude was then purified by flash chromatography to yield 6.0 g (85% yield) of (xvi).

Step 17

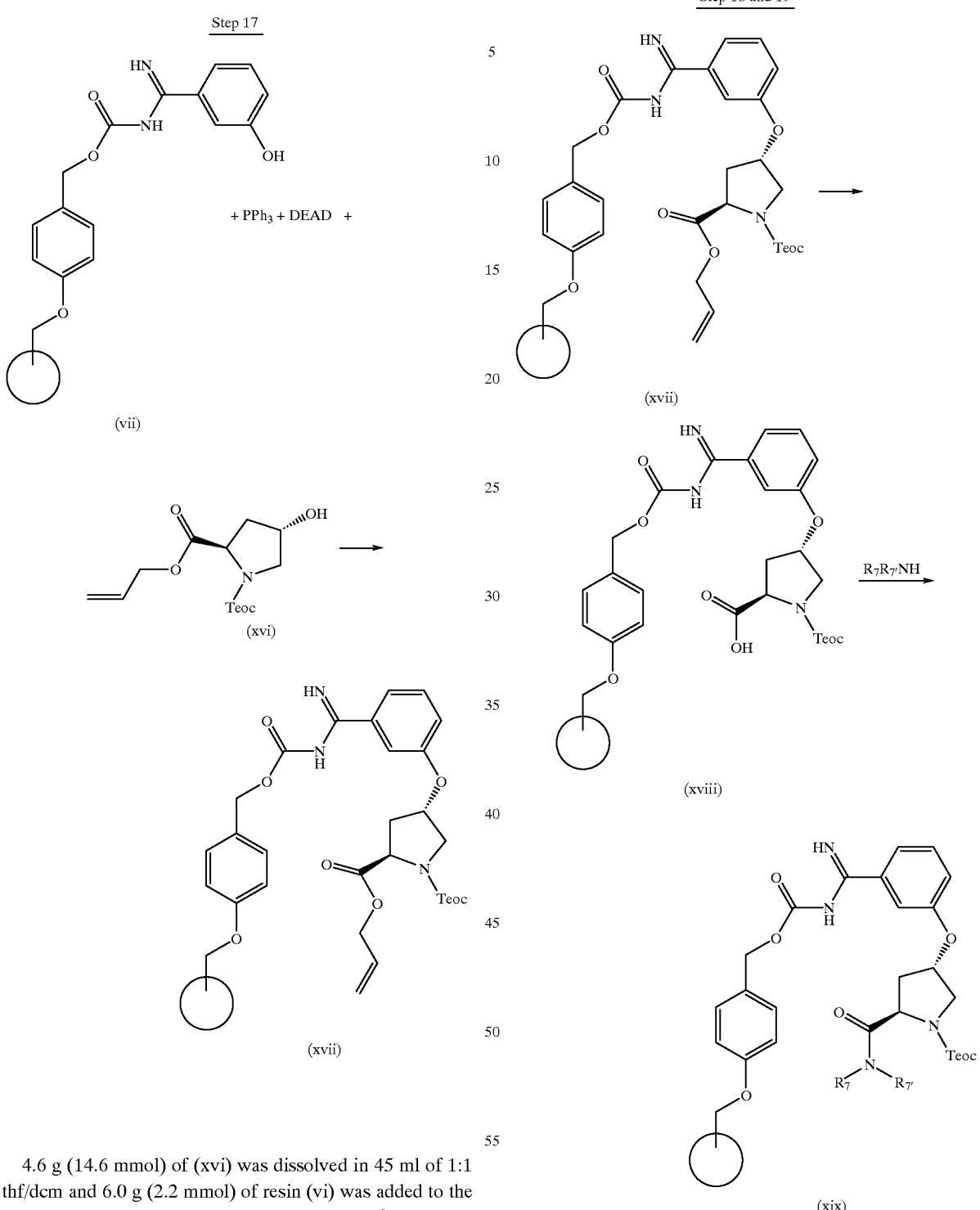

4.6 g (14.6 mmol) of (xvi) was dissolved in 45 ml of 1:1 thf/dcm and 6.0 g (2.2 mmol) of resin (vi) was added to the solution. The suspension was then cooled to 0° C. 2.4 ml (15.0 mmol) of DEAD was added to the suspension at 0° C., followed by an addition of 4.0 g (14.6 mmol) of triphenylphosphine. The reaction was then allowed to warm to room temperature and stirred overnight. The resin was drained and washed twice with thf, twice with 20% acetic acid in dcm, twice with methanol, and twice with dcm to afford resin (xvii).

Allyl deprotection and subsequent amine and aniline addition to the carboxylic acid moiety was performed using the procedures described in steps 10–12 to generate resin type (xix).

Step 20

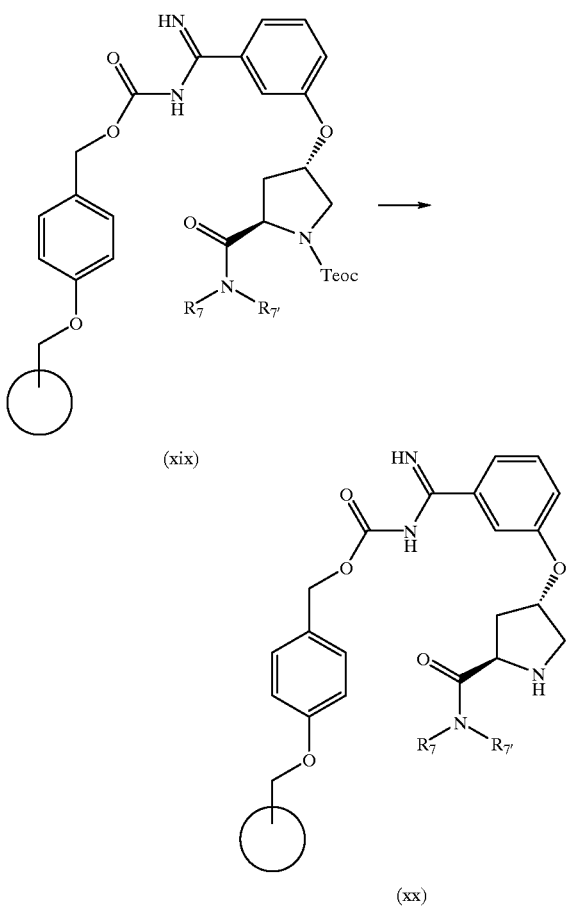

(xix)

(xx)

100 mg of resins of type (xix) were then suspended in 2.0 ml of thf and to this suspension was added 1.0 ml of 1.0 M tbaf in thf. The reactions were agitated for 1 hour, following by a draining. The resins were then washed three times with thf, three times with 20% acetic acid in dcm, three times with methanol, and three times with dcm to generate resins of type (xx).

Step 21

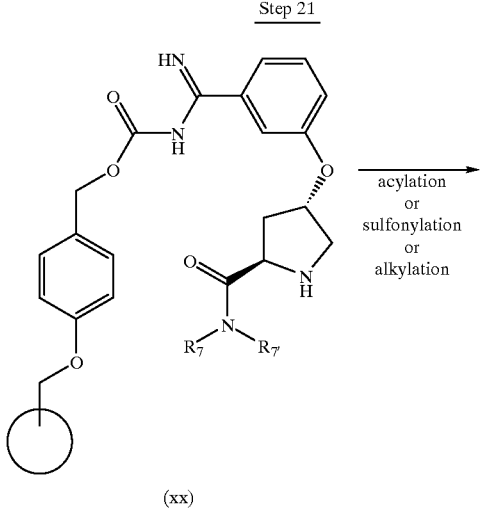

(xx)

acylation or sulfonylation or alkylation

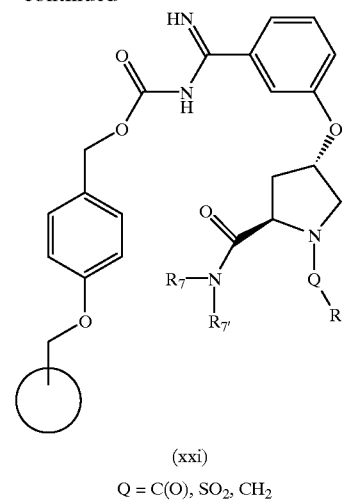

(xxi)

Q = C(O), SO$_2$, CH$_2$

Resins of type (xx) were then acylated, sulfonylated, and alkylated according to the following procedures: 1) Acylation: In a separate 20 ml scintillation vial, 3.0 ml of 0.3 M solutions of selected carboxylic acid, HBTU, HOBt, and dipea in dimethylacetamide were prepared and agitated on a shaker for 10 min. These cocktails were then added directly to 100 mg of type (B) resins loaded into Quest RV's. The reactions were then agitated for 30 min, drained, and washed three times with dma, methanol, and dichloromethane. 2) Sulfonylation: 100 mg of type (B) resin was loaded into Quest RV's and resins were suspended in 3.0 ml of thf. To the suspensions were added 1.0 mmol of the selected sulfonyl chloride and 1.0 mmol of dipea. The reactions were agitated for 30 min. and drained, washed three times with dma, three times with methanol, and three times with dcm. 3) Alkylation: To 100 mg of type (B) resin loaded into Quest RV's was added 1.0 mmol of the selected aldehyde in 3.0 ml of 1% acetic acid in dmf. The reaction was agitated for 30 min., followed by an addition of 1.3 mmol of Sodium cyanoborohydride as a powder. The reactions were agitated for an additional two hours, followed by a draining. The resins were then washed three times with methanol, twice with 20% acetic acid in dcm, twice with methanol, and twice with dcm to afford resins of class (xxi).

Step 22

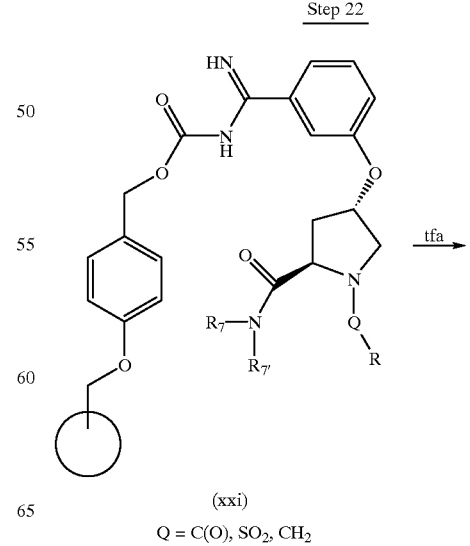

(xxi)

Q = C(O), SO$_2$, CH$_2$ tfa

-continued

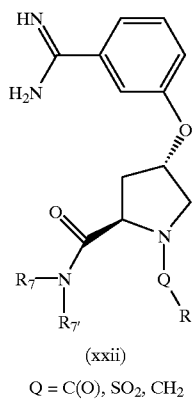

(xxii)

Q = C(O), SO₂, CH₂

Type (xxi) resins were then cleaved by treatment with 3.0 ml of straight tfa. The tfa cleavage cocktails were collected into scintillation vials and the resins were rinsed with one 3.0 ml portion of tfa. The samples were then concentrated by vacuum and submitted for reverse phase HPLC purification.

EXAMPLE 2

Tissue Factor/Factor VIIa Antagonist Assay

This procedure is used to determine the constant of inhibition (Ki) for a sample compound of the invention.

Materials

Assay Buffer: 100 mM Hepes pH 7.8, 140 mM NaCl, 0.1% PEG-8000, 0.02% Tween-80, 5 mM CaCl₂

Coagulation Factor: recombinant human factor VIIa (NB #25942-16)

Cofactor: soluble Tissue Factor (1-219)

Substrate: Chromozym-tPA (Boehringer Mannheim, Cat. #1093 037) Reconstitute at 20 mM in H₂O. Dilute to 4 mM in assay buffer with CaCl₂ prior to use.

Samples: Dilute samples to 3% DMSO in assay buffer (lacking CaCl₂).

Procedure
1. Prepare a solution of 2 μg/mL (90 nM) tissue factor and 1.5 μg/mL (30 nM) factor VIIa in assay buffer with CaCl₂.
2. Incubate for 15 minutes at room temperature.
3. Add 50 μL sample to each well.
4. Add 50 μL tissue factor/factor VIIa solution to each well.
5. Incubate for 15 minutes at room temperature with gentle agitation.
6. Add 50 μL substrate to each well.
7. Agitate plate for 20–25 sec.
8. Monitor absorbance at 405 nM every 10 sec for a total of 5 minutes at room temperature.
9. Calculate Vmax over 10 points.

EXAMPLE 3

Factor Xa, Thrombin, and Plasma Kallikrein Assays

These procedures are used to determine the constant of inhibition (Ki) for a sample compound of the invention.

Materials

Assay Buffer: 100 mM Hepes pH 7.8, 140 mM NaCl, 0.1% PEG-8000, 0.02% Tween-80

Coagulation Factor: human Factor Xa, Thrombin, or Plasma Kallikrein (Hematologic Technologies) Dilute to 0.45 μg/mL (9.8 nM) in assay buffer.

Substrate: S-2222, S2366 or S2302—(See below—Chromogenix Inc,) Reconstitute at 5 mM in H2O. Dilute to 1.5 mM in assay buffer prior to use.

Samples: Dilute samples to 3% DMSO in assay buffer.

Procedure
1. Add 50 μL sample to each well.
2. Add 50 μL appropriately diluted coagulation factor to each well.
3. Incubate for 5 minutes at room temperature with gentle agitation.
4. Add 50 μL appropriately diluted substrate to each well.
5. Agitate plate for 20–25 sec.
6. Monitor absorbance at 405 nM every 10 sec for a total of 5 minutes at room temperature.
7. Calculate Vmax over 10 points.

TABLE 1 enzyme, substrate and final concentrations

| Assay | TF/VIIa | Xa | thrombin | plasma kallikrein |
| --- | --- | --- | --- | --- |
| coag factor final concentration | 10 nM VIIa 30 nM TF | 3.3 nM | 8.2 nM | 1.5 nM |
| substrate | Chromozyme tPA | S-2222 | S-2366 | S-2302 |
| final conc. of substrate | 1.33 mM | 0.5 mM | 0.3 mM | 0.3 mM |

TABLE 2 binding affinity to serine proteases

| cmpd | VIIa (μm) | Xa (μm) | thrombin (μm) | trypsin (μm) | plasmin (μm) | kallikrein (μm) |
| --- | --- | --- | --- | --- | --- | --- |
| 1 | 7.8 | 0.297 | 4.744 | 0.866 | 7.36 | 6.559 |
| 2 | 64 | 1.15 | | | | |
| 3 | 234 | 1.294 | 4.221 | 1.127 | 10.881 | 14.219 |
| 4 | >39 | 1.455 | 14.5 | 2.81 | 3.5 | 14 |
| 5 | >39 | 2.134 | 14.5 | 2.136 | 7 | 16 |
| 6 | >39 | 2.414 | 36 | 5.146 | 15 | 3.4 |
| 7 | >39 | 2.491 | 25 | 2.22 | 7 | 20 |
| 8 | 390 | 3.32 | | | | |
| 9 | 390 | 5.13 | | | | |
| 10 | 98.5 | 5.35 | | | | |
| 11 | 39 | 5.845 | 0.875 | 0.607 | 7.358 | 0.979 |
| 12 | 156 | 6.02 | | | | |
| 13 | 390 | 6.12 | | | | |
| 14 | >39 | 6.613 | >36.2 | 10.145 | >24.5 | 33.8 |
| 15 | 156 | 6.796 | 11.025 | 2.259 | 15.369 | 34.214 |
| 16 | >39 | 6.81 | 29 | 6.066 | 12 | 17 |
| 17 | >39 | 7.879 | 36.2 | 3.597 | 24.5 | >33.8 |
| 18 | 273 | 8.87 | | | | |
| 19 | 312 | 9 | | | | |
| 20 | 234 | 9.07 | | | | |
| 21 | >39 | 10.5 | 14.5 | 20.2 | 24.5 | 33.8 |
| 22 | >39 | 10.5 | >36 | 7.762 | 15 | 3.4 |
| 23 | >195 | 11.964 | | | | |
| 24 | 312 | 12.92 | | | | |
| 25 | 156 | 13.29 | | | | |
| 26 | 142.18 | 113.69 | | | | |
| 27 | 15.6 | 14.026 | 36.17 | 14.134 | >24.58 | |
| 28 | 390 | 14.1 | | | | |
| 29 | 117 | 14.24 | | | | |
| 30 | 312 | 15.19 | | | | |
| 31 | 390 | 15.2 | | | | |
| 32 | >399 | 15.26 | 36.2 | 7.84 | 24.5 | 33.8 |
| 33 | 30.5 | 15.53 | | | | |
| 34 | 156 | 16.785 | | | | |
| 35 | 93.95 | 19.73 | | | | |
| 36 | >195 | 19.854 | 21.7 | 4.256 | 24.5 | >33.8 |
| 37 | >39 | 14 | | | | |
| | 312 | 21.68 | | | | |

TABLE 2-continued binding affinity to serine proteases

| cmpd | VIIa (μm) | Xa (μm) | thrombin (μm) | trypsin (μm) | plasmin (μm) | kallikrein (μm) |
|---|---|---|---|---|---|---|
| 38 | 129 | 21.69 | | | | |
| 39 | 390 | 22.8 | | | | |
| 40 | 156 | 22.97 | | | | |
| 41 | 187 | 24.26 | | | | |
| 42 | 89 | 24.37 | | | | |
| 43 | 156 | 24.53 | | | | |
| 44 | 117 | 25.9452 | | | | |
| 45 | 150 | 26.31 | | | | |
| 46 | 156 | 27.03 | | | | |
| 47 | 390 | 31.43 | | | | |
| 48 | >195 | 33.596 | | | | |
| 49 | 390 | 33.82 | | | | |
| 50 | >195 | 34.122 | | | | |
| 51 | 234 | 35.1 | | | | |
| 52 | >39 | 35.1 | >36.2 | 40.5 | >24.5 | 27.02 |
| 53 | 133 | 37.13 | | | | |
| 54 | 390 | 38 | | | | |
| 55 | 273 | 44.91 | | | | |
| 56 | >195 | 47.268 | | | | |
| 57 | 312 | 49.3 | | | | |
| 58 | 390 | 50.7 | | | | |
| 59 | 390 | 59.82 | | | | |
| 60 | >195 | 61.223 | 36.2 | 4.989 | 24.5 | 33.8 |
|    | >39   | 21 | | | | |
| 61 | 195 | 61.99 | | | | |
| 62 | >390 | 64.58 | | | | |
| 63 | 390 | 70 | | | | |
| 64 | 273 | 70.1 | | | | |
| 65 | 30.71 | 70.1 | | | | |
| 66 | 78 | 70.1 | | | | |
| 67 | 390 | 87.7 | | | | |
| 68 | 390 | 89.62 | | | | |
| 69 | 117 | 90.22 | | | | |
| 70 | 156 | 105 | | | | |
| 71 | 390 | 105 | | | | |
| 72 | 390 | 132 | | | | |
| 73 | 390 | 140 | | | | |
| 74 | >195 | 140 | | | | |
| 75 | 390 | 140 | | | | |
| 76 | >195 | 175 | >36.2 | 30.272 | >24.5 | >33.8 |
|    | >39  | 35.1 | | | | |
| 77 | >390 | 175 | | | | |
| 78 | >195 | 175 | | | | |
| 79 | 19 | >35 | >36 | 20 | 24 | |
| 80 | >39 | >35.1 | >36.17 | 28.3 | >24.58 | 54.96 |
| 81 | >195 | >175 | | | | |
| 82 | >195 | >175 | | | | |

We claim:
1. A compound of formula (I)

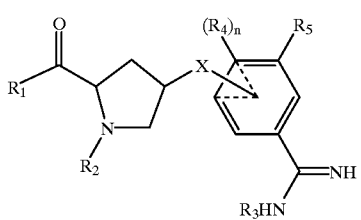

wherein
X is O, $CR_6R_{6'}$, $NR_6$ or S, wherein $R_6$ and $R_{6'}$ are independently H or alkyl;
$R_1$ is H, $-OR_7$, an amino acid or $-NR_7R_{7'}$, wherein $R_7$ and $R_{7'}$ are independently H or a hydrocarbon chain, a carbocycle, a heterocycle, a carbocycle-substituted hydrocarbon chain or a heterocycle-substituted hydrocarbon chain optionally substituted with hydroxyl, halogen, cyano, amino, nitro, amidine, guanidine alkyl, halo-substituted alkyl, alkoxy, aryl or carboxyl; or $R_7$ and $R_{7'}$ together form a heterocycle optionally fused to another heterocycle or carbocycle wherein said heterocycle and carbocycle are optionally substituted with hydroxyl, halogen, amino, nitro, amidine, guanidine, alkyl, halo-substituted alkyl, alkoxy or carboxyl;

$R_2$ is H or a hydrocarbon chain, a carbocycle or a carbocycle-substituted hydrocarbon chain optionally substituted with hydroxyl, oxo, halogen, cyano, amino, nitro, amidine, guanidine, alkyl, halo-substituted alkyl, alkoxy or carboxyl; and wherein said hydrocarbon chain is optionally interrupted with N, O, S, SO or $SO_2$;

$R_3$ is H or a protecting group;

$R_4$ is selected from the group consisting of H, hydroxyl, halogen, amino, nitro, amidine, guanidine and acylamino;

$R_5$ is H or $R_4$ and $R_5$ together form a 5 or 6 member carbocycle or heterocycle ring optionally substituted with hydroxyl, halogen, amino, nitro, amidine, guanidine or acylamino;

n is 0 or 1; or a salt, a solrate or a hydrate thereof.

2. A compound according to claim 1, wherein X is O.
3. A compound according to claim 1, wherein X is $CH_2$.
4. A compound according to claim 1, wherein $R_1$ is an amino acid or $-NR_7R_{7'}$, wherein $R_7$ and $R_{7'}$ are independently H or a hydrocarbon chain, a carbocycle, a heterocycle, a carbocycle-substituted hydrocarbon chain or a heterocycle-substituted hydrocarbon chain optionally substituted with hydroxyl, halogen, cyano, amino, nitro, amidine, guanidine alkyl, halo-substituted alkyl, alkoxy, aryl or carboxyl; or $R_7$ and $R_{7'}$ together form a heterocyle optionally fused to another heterocycle or carbocycle wherein said heterocycle and carbocycle are optionally substituted with hydroxyl, halogen, amino, nitro, amidine, guanidine, alkyl, halo-substituted alkyl, alkoxy or carboxyl.

5. A compound according to claim 4, wherein $R_1$ is $NR_7R_{7'}$ and $R_7$ is a aryl or aralkyl optionally substituted with hydroxyl, halogen, amino, amidine, guanidine, cyano, alkyl, alkoxy, halo-substituted alkyl; and $R_{7'}$ is H or alkyl.

6. A compound according to claim 4, wherein $R_1$ is $NR_7R_{7'}$ and $R_7$ is phenyl or benzyl substituted with amidine or alkoxy; and $R_{7'}$ is H or methyl.

7. A compound according to claim 4, wherein $R_1$ is $NR_7R_{7'}$ and $R_7$ and $R_{7'}$ together form a heterocyle optionally fused to another heterocycle or carbocycle wherein said heterocycle and carbocycle are optionally substituted with hydroxyl, halogen, amino, nitro, amidine, guanidine, alkyl, halo-substituted alkyl, alkoxy or carboxyl.

8. A compound according to claim 4, wherein $R_7$ is benzyl, p-amidinylphenyl, p-methoxybenzyl or p-methylbenzyl and $R_{7'}$ is H.

9. A compound according to claim 8, wherein $R_7$ and $R_{7'}$ together form a piperidine ring fused to a benzene ring wherein said fused benzene ring is optionally substituted with alkoxy.

10. A compound according to claim 9, wherein said fused benzene ring is substituted at both beta carbon positions with methoxy.

11. A compound according to claim 1, wherein $R_2$ is H, alkyl, cycloalkyl, aryl, cycloalkylalkyl or aralkyl optionally substituted with alkyl, amino, amidine, guanidine or nitro.

12. A compound according to claim 11, wherein $R_2$ is H, alkyl, aryl, aralkyl or cycloalkyl.

13. A compound according to claim 11, wherein $R_2$ is propyl, phenylethyl, cyclohexyl, o-nitrobenzyl or m-methylbenzyl.

14. A compound according to claim 1, wherein $R_3$ is H.

15. A compound according to claim 1, wherein n is 1 and $R_4$ is H, hydroxyl, amino or alkanoylamino.

16. A compound according to claim 15, wherein n is 1 and $R_4$ and $R_5$ are both H.

17. A compound according to claim 1, wherein $R_4$ and $R_5$ together form a benzene ring.

18. A method of inhibiting binding of a serine protease to a protein ligand comprising contacting said serine protease with a compound of claim 1.

19. A method of treating a disease or condition mediated by a serine protease in a mammal comprising administering to said mammal an effective amount of a compound according to claim 1.

20. A method of inhibiting veinous or arterial thrombus formation in a mammal comprising administering to said mammal an effective amount of a compound according to claim 1.

* * * * *

UNITED STATES PATENT AND TRADEMARK OFFICE
CERTIFICATE OF CORRECTION

PATENT NO.    : 6,410,733 B1
DATED         : June 25, 2002
INVENTOR(S)   : Richard M. Pastor et al.

It is certified that error appears in the above-identified patent and that said Letters Patent is hereby corrected as shown below:

Column 52,
Line 22, please delete "solrate" and insert -- solvate --.

Signed and Sealed this

Twentieth Day of August, 2002

Attest:

JAMES E. ROGAN
Attesting Officer    Director of the United States Patent and Trademark Office